US011744899B2

(12) United States Patent
Takahata et al.

(10) Patent No.: US 11,744,899 B2
(45) Date of Patent: Sep. 5, 2023

(54) PHARMACEUTICAL COMPOSITION CONTAINING A HYALURONIC ACID DERIVATIVE

(71) Applicant: SEIKAGAKU CORPORATION, Tokyo (JP)

(72) Inventors: Chiaki Takahata, Tokyo (JP); Naoya Yamashita, Tokyo (JP); Naoko Kunii, Tokyo (JP); Hirotaka Hoshi, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 250 days.

(21) Appl. No.: 17/276,263

(22) PCT Filed: Nov. 15, 2019

(86) PCT No.: PCT/JP2019/044851
§ 371 (c)(1),
(2) Date: Mar. 15, 2021

(87) PCT Pub. No.: WO2020/101013
PCT Pub. Date: May 22, 2020

(65) Prior Publication Data
US 2022/0016255 A1   Jan. 20, 2022

(30) Foreign Application Priority Data

Nov. 16, 2018 (JP) ................... 2018-215867

(51) Int. Cl.
| | |
|---|---|
| *A61K 47/61* | (2017.01) |
| *A61K 47/55* | (2017.01) |
| *A61P 19/02* | (2006.01) |
| *A61K 47/02* | (2006.01) |
| *A61K 47/10* | (2017.01) |
| *A61K 47/26* | (2006.01) |
| *A61K 47/40* | (2006.01) |
| *A61K 9/00* | (2006.01) |
| *A61K 9/08* | (2006.01) |
| *A61M 5/178* | (2006.01) |

(52) U.S. Cl.
CPC ............ *A61K 47/61* (2017.08); *A61K 9/0019* (2013.01); *A61K 9/08* (2013.01); *A61K 47/02* (2013.01); *A61K 47/10* (2013.01); *A61K 47/26* (2013.01); *A61K 47/40* (2013.01); *A61K 47/55* (2017.08); *A61P 19/02* (2018.01); *A61M 5/178* (2013.01)

(58) Field of Classification Search
CPC ...... A61K 31/728; A61K 47/10; A61K 47/20; A61K 47/26; A61K 47/34; A61K 47/40; A61K 47/61
See application file for complete search history.

(56) References Cited

U.S. PATENT DOCUMENTS

| | | |
|---|---|---|
| 2008/0221062 A1 | 9/2008 | Miyamoto et al. |
| 2011/0083991 A1 | 4/2011 | Miyamoto et al. |
| 2016/0151506 A1 | 6/2016 | Miyamoto et al. |
| 2018/0360980 A1 | 12/2018 | Miyamoto et al. |
| 2019/0008891 A1 | 1/2019 | Nogami et al. |
| 2019/0184023 A1 | 6/2019 | Miyamoto et al. |
| 2020/0129541 A1 | 4/2020 | Kano et al. |

FOREIGN PATENT DOCUMENTS

| | | |
|---|---|---|
| JP | 10-212303 A | 8/1998 |
| WO | 2005/066214 A1 | 7/2005 |
| WO | 2015/005458 A1 | 1/2015 |
| WO | 2015/128787 A1 | 9/2015 |
| WO | 2017/131130 A1 | 8/2017 |
| WO | 2018/168920 A1 | 9/2018 |

OTHER PUBLICATIONS

Falcone S. et al "Rheological and cohesive properties of hyaluronic acid" J. Biomed. Mater. Res. Part A an Official Journal of the Society for Biomaterials, the Japanese Society for Biomaterials, and the Australian Society for Biomaterials and the Korean Society for Biomaterials, vol. 76, No. 4, pp. 721 (Year: 2006).*
Yoshioka et al. "Pharmacological effects of N-[2-[[2-[2[(2,6-dichlorophenyl)aminolphenyl]acetyl]oxy]ethyl]hyaluronamide (diclofenac Etalhyaluronate, SI-613), a novel sodium hyaluronate derivatie chemically linked with diclofenac", BMC Musculoskeletal Disorders (2018) 19:157.
International Search Report issued in International Patent Application No. PCT/JP2019/044851, dated Jan. 21, 2020, along with an English translation thereof.
Written Opinion of the International Searching Authority issued in International Application No. PCT/JP2019/044851, dated Jan. 21, 2020, along with an English translation thereof.

* cited by examiner

*Primary Examiner* — Leigh C Maier
(74) *Attorney, Agent, or Firm* — GREENBLUM & BERNSTEIN, P.L.C.

(57) ABSTRACT

Provided is a method for suppressing the generation of diclofenac lactam from a compound represented by a formula (1) in the description, including allowing the compound of the formula (1) and a component (A) that is at least one type of compound selected from the group consisting of a nonionic surfactant, a hydroxyalkylated cyclodextrin, a C1 to C3 mono-alcohol, a C2 to C3 di-alcohol, a C3 to C6 tri-alcohol, a polyalkylene glycol, a γ-lactone, polyvinylpyrrolidone, a chlorogenic acid, and an alkyl sulfate ester, and salts thereof to coexist. A method for producing a pharmaceutical composition containing a compound represented by the formula (1) and a component (A), and a pharmaceutical composition which is a product produced thereby are also provided.

13 Claims, No Drawings

PHARMACEUTICAL COMPOSITION CONTAINING A HYALURONIC ACID DERIVATIVE

TECHNICAL FIELD

The present invention relates to a pharmaceutical composition containing a hyaluronic acid derivative.

BACKGROUND ART

Osteoarthritis (hereinafter, also referred to as "OA" in the present description), which is dysfunction caused by joint pain or joint degeneration, is the most common joint disease in the whole world, and is one of the major causes of a physical disorder that interferes with daily life especially in the elderly. Further, rheumatoid arthritis (hereinafter also referred to as "RA" in the present description), which is polyarthritis, is known as a disease accompanied by swelling and pain in joints similar to OA. Also in RA, if the disease state continues for a long period of time and the symptom progresses, cartilages and bones are destroyed and degenerative deformation occurs, resulting in a physical disorder that interferes with daily life such as narrowing of the joint range of motion.

At present, a drug formulation using hyaluronic acid or a derivative thereof is used as a medicine for a joint disease such as osteoarthritis or rheumatoid arthritis. A hyaluronic acid formulation is usually formulated as an injection, and for the purpose of improving dysfunction caused by a joint disease and suppressing pain through a lubricating action, an impact absorbing action, a cartilage metabolism improving action, or the like of hyaluronic acid, the hyaluronic acid formulation is directly administered to a joint of a knee, a shoulder, or the like that is an affected part. The hyaluronic acid formulation that has been made into a product includes, for example, those containing purified sodium hyaluronate as an active ingredient (for example, ARTZ (registered trademark) and SUVENYL (registered trademark)). The drug formulation is required to be administered 3 to 5 consecutive times at a frequency of once a week.

Further, as a drug formulation containing cross-linked hyaluronic acid as an active ingredient, those required to be administered 3 consecutive times at a frequency of once a week (for example, Synvisc (registered trademark)), and those for single administration, with which a treatment is completed by single administration (for example, Synvisc-One (registered trademark), Gel-One (registered trademark), and MONOVISC (registered trademark)) are known.

On the other hand, steroids and non-steroidal anti-inflammatory compounds are known as fast-acting drugs, and are also used in a treatment aiming at relieving joint pain caused by OA or RA, or the like. For example, triamcinolone acetonide that is a steroid has been on the market as a drug for intra-articular injection for a treatment of a joint disease such as rheumatoid arthritis, and in the treatment, it is necessary to administer the drug every one to two weeks. In addition, as the non-steroidal anti-inflammatory compound, for example, an ointment or an orally administered agent containing diclofenac sodium as an active ingredient is known, and it is necessary to administer the drug a plurality of times per day in order to exhibit an anti-inflammatory effect.

It is also known that a mixture or a conjugate of hyaluronic acid or a derivative thereof and a steroid or a non-steroidal anti-inflammatory compound is used as an active ingredient. For example, a mixture of crosslinked hyaluronic acid and triamcinolone hexacetonide (CINGAL (registered trademark)) has been made into a product as a drug for single administration. Further, a compound in which hyaluronic acid or a derivative thereof and a steroid or a non-steroidal anti-inflammatory compound are linked to each other is also known. For example, Patent Literature 1 and Patent Literature 2 describe derivatives in which an anti-inflammatory compound is introduced into hyaluronic acid via a spacer. These aim at both rapid-acting pain relief and long-term pain relief through improvement of dysfunction, however, these are in the middle of development and have not been put on the market as an approved drug.

In addition, as another example, the development of a conjugate in which diclofenac that is an anti-inflammatory compound is introduced into a sugar chain of hyaluronic acid at a certain ratio (hereinafter sometimes referred to as "Dic-HA") aiming at both rapid-acting pain relief and long-term pain relief through improvement of dysfunction has been advanced. However, Dic-HA is also still in the middle of development.

As a technique for stabilizing hyaluronic acid, Patent Literature 3 discloses a method of adding an iodine-containing reducing agent and/or a sulfur-containing reducing agent to hyaluronic acid. Further, Patent Literature 4 discloses that an aqueous composition containing hyaluronic acid is stabilized by sorbitol.

CITATION LIST

Patent Literature

Patent Literature 1: WO 2005/066214
Patent Literature 2: WO 2015/005458
Patent Literature 3: JP-A-10-212303
Patent Literature 4: WO 2017/131130

SUMMARY OF INVENTION

Diclofenac produced from Dic-HA is a low-molecular compound, and therefore is hardly retained at the administration site (for example, the synovial membrane in a joint), and transfers to a site other than the administration site such as a lymph or blood at an early stage. Therefore, the generation of diclofenac in a pharmaceutical composition before administration into the body is not preferred from the viewpoint of long-term sustainability of drug efficacy. However, the behavior in which diclofenac is generated from Dic-HA is not clear, and it was unknown whether there is a practical need to prevent the generation in the first place, and if there is a need, how the generation can be prevented.

When the present inventors advanced the development, the presence of a decomposition product of Dic-HA was observed in a Dic-HA-containing composition. Then, when the decomposition product was analyzed, it was found that a molecule produced from Dic-HA is contained in the composition not only as diclofenac, but also as diclofenac lactam. Further, it was found that the accumulation amount of diclofenac lactam is increased with a storage period or a heating treatment or the like.

When the present inventors advanced the study, diclofenac itself is a physiologically active substance having an anti-inflammatory effect, but the Cox-2 inhibitory activity of diclofenac lactam that is a lactam form thereof is about $\frac{1}{100}$ of that of diclofenac, and diclofenac lactam was not regarded as a physiologically active anti-inflammatory substance. As a result, the significance of suppressing the generation of physiologically inactive diclofenac lactam and providing a composition in which the accumulation of diclofenac lactam is suppressed was more clearly found out.

As a technique for stabilizing hyaluronic acid, Patent Literature 3 discloses a method of adding an iodine-containing reducing agent and/or a sulfur-containing reducing agent to hyaluronic acid, however, these reducing agents are agents that suppress a decrease in the molecular weight of hyaluronic acid, and suppression of the generation of a diclofenac component from a hyaluronic acid conjugate is not described or suggested. Further, Patent Literature 4 discloses that an aqueous composition containing hyaluronic acid is stabilized by sorbitol, however, what is used as an index here is suppression of a decrease in the viscosity of the aqueous composition, and therefore, it is understood that the stabilization here is suppression of a decrease in the molecular weight of hyaluronic acid. That is, suppression of the generation of a diclofenac component from a hyaluronic acid conjugate such as Dic-HA is not described or suggested.

As described above, there exists a report regarding a stabilization technique related to suppression of a decrease in the molecular weight of hyaluronic acid, however, there existed no finding regarding a technique for suppressing the generation of diclofenac lactam due to decomposition of Dic-HA. The present inventors found conflicting problems regarding decomposition performance that diclofenac having a physiological activity as an anti-inflammatory agent is desired to be released in a controlled manner by slowly decomposing Dic-HA in the body of a patient after administration while suppressing the decomposition of Dic-HA at a stage before administration to the patient as a medicine (suppressing the accumulation of diclofenac lactam), but were in a state where no solution guidelines were provided from the prior art.

One aspect of the present invention relates to a pharmaceutical composition containing a compound represented by the following formula (1) and further containing a component (A) that is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof. The pharmaceutical composition is favorably used as a treatment agent for topical administration (for example, an anti-inflammatory agent or a pain inhibitor), and is particularly preferably used as a composition for treating a joint disease such as OA or RA. Another aspect of the present invention relates to a method for producing the pharmaceutical composition including a step of allowing a compound represented by the following formula (1) and the component (A) to coexist. Still another aspect of the present invention relates to a method for suppressing the generation of diclofenac lactam from a compound represented by the following formula (1) including a step of allowing the component (A) to coexist with the compound represented by the following formula (1). Yet still another aspect of the present invention relates to a method for suppressing the generation of a diclofenac component from a compound represented by the following formula (1) including a step of allowing the component (A) to coexist with the compound represented by the following formula (1).

Another aspect of the present invention relates to an aqueous composition containing a compound represented by the following formula (1) and showing a maximum treatment amount ($V_{max}$) of 1.0 g/cm² or more.

[Chem. 1]

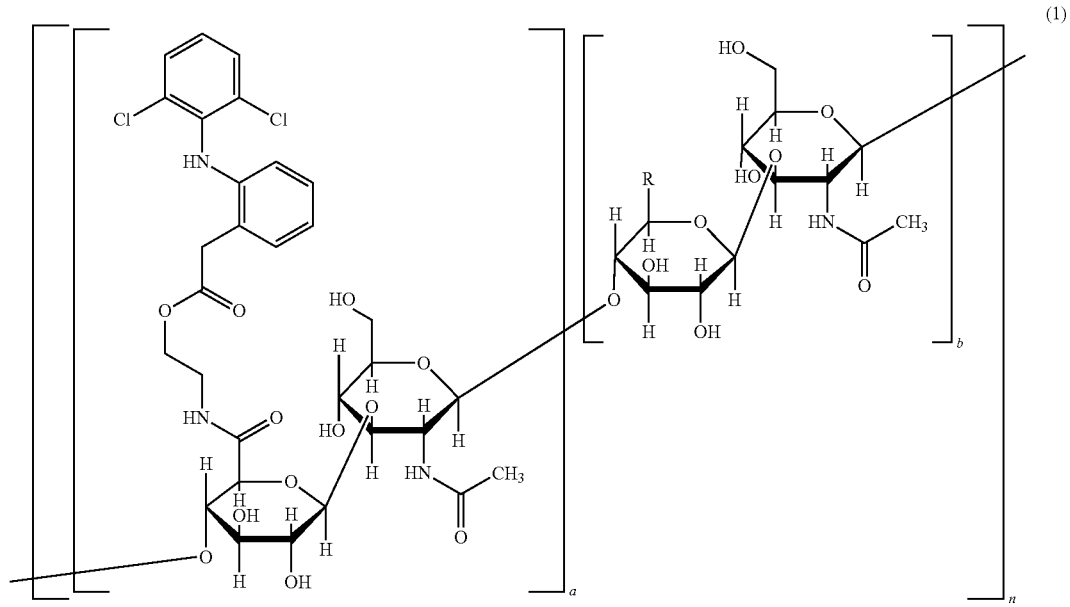

(1)

The present inventors found that by allowing a certain type of compound to coexist in a Dic-HA-containing composition or enhancing the filterability of the Dic-HA-containing aqueous composition, the accumulation amount of diclofenac lactam in the Dic-HA-containing composition can be suppressed.

Note that in the formula (1), a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

In the present description, the compound represented by the above formula (1) is sometimes expressed as "hyaluronic acid derivative". Further, in the formula (1), the constituent disaccharide unit present at a ratio of a is also referred to as "diclofenac-introduced constituent disaccharide unit", and the constituent disaccharide unit present at a ratio of b is also referred to as "hyaluronic acid constituent disaccharide unit" (that is, a structure in which N-acetyl-D-glucosamine and D-glucuronic acid or a salt thereof are linked via a β-(1,3) linkage). Further, the "diclofenac-introduced constituent disaccharide unit" and the "hyaluronic acid constituent disaccharide unit" are also simply referred to as "constituent disaccharide unit" without particularly distinguishing them.

In the present description, the component (A) and a filterability improving agent are also collectively referred to as "additional component".

As more specific examples, the present invention relates to the following [1] to [23].

[1] A pharmaceutical composition, containing a compound represented by the formula (1) and a component (A), wherein the component (A) is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof.

[2] The pharmaceutical composition according to the above [1], which is for use in a treatment of a joint disease.

[3] A kit, including an injector in which the pharmaceutical composition according to the above [1] or [2] is filled in a syringe barrel.

[4] A kit, including a vial containing the pharmaceutical composition according to the above [1] or [2], and an injector.

[5] A method for producing a pharmaceutical composition containing a compound represented by the formula (1), including a step of allowing the compound represented by the formula (1) and the component (A) to coexist.

[6] A method for suppressing the generation of diclofenac lactam from a compound represented by the formula (1), including a step of allowing the component (A) to coexist with the compound represented by the formula (1).

[7] Use of a component (A) in the production of a pharmaceutical composition containing a compound represented by the formula (1), including a step of allowing the component (A) and the compound represented by the formula (1) to coexist, wherein the pharmaceutical composition is for use in a treatment of a joint disease, and the component (A) is a compound that suppresses the generation of diclofenac lactam from the compound represented by the formula (1).

[8] A component (A), which is for use in a treatment of a human joint disease, and is used as a constituent component of a pharmaceutical composition for treating a joint disease together with a compound represented by the formula (1).

[9] A method for treating a human joint disease, including a step of administering a pharmaceutical composition to a joint of a patient with a joint disease, wherein the pharmaceutical composition is a pharmaceutical composition containing an effective amount of a compound represented by the formula (1) and a component (A).

[10] An aqueous composition, containing a compound represented by the formula (1), wherein a maximum treatment amount ($V_{max}$) of the aqueous composition is 1.0 g/cm$^2$ or more, provided that the maximum treatment amount ($V_{max}$) is a value derived by filtering the aqueous composition at a liquid temperature of 70° C. under a pressure of 0.6 MPa using a polyvinylidene fluoride filtration membrane with a pore size of 0.22 μm, measuring the total filtration amount per effective filtration area every 30 seconds until the flow rate becomes 1/10 or less of the flow rate at the start of filtration, and substituting the thus obtained measurement value for the following calculation formulae A and B:

$$\text{Calculation Formula A: } t/V = at + b \quad [\text{Math. 1}]$$

$$\text{Calculation Formula B: } V_{max} = 1/a \quad [\text{Math. 2}]$$

wherein t represents the filtration time (min), V represents the total filtration amount per effective filtration area (g/cm$^2$), a represents the slope of the calculation formula A, and b represents the intercept of the calculation formula A.

[11] The aqueous composition according to the above [10], further containing a filterability improving agent.

[12] The aqueous composition according to the above [11], wherein the filterability improving agent is selected from the group consisting of a polyalkylene glycol, a $C_1$ to $C_3$ mono-alcohol, a hydroxyalkylated cyclodextrin, and salts thereof.

[13] The aqueous composition according to the above [11] or [12], wherein the relative amount of diclofenac lactam measured under the following conditions is 0.9 or less (for example, 0.8 or less or 0.75 or less):

after each of a test composition in which the compound represented by the formula (1) and the filterability improving agent are allowed to coexist, and a control composition having the same formulation as the test composition except that the filterability improving agent is not contained is stored for 1 week in a thermostat bath at 60° C., the amount of diclofenac lactam accumulated in the test composition and the control composition is measured by high performance liquid chromatography, and the amount of diclofenac lactam accumulated in the test composition is calculated as a relative amount when the amount of diclofenac lactam accumulated in the control composition is assumed to be 1.

[14] The aqueous composition according to any one of the above [11] to [13], wherein the relative amount of diclofenac measured under the following conditions is less than 1 (for example, 0.95 or less or 0.9 or less):

after each of a test composition in which the compound represented by the formula (1) and the filterability improving agent are allowed to coexist, and a control composition having the same formulation as the test composition except that the filterability improving agent is not contained is stored for 1 week in a thermostat bath at 60° C., the amount of diclofenac accumulated in the test composition and the control composition is measured by high performance liquid chromatography, and the amount of diclofenac accumulated in the test composition is calculated as a relative amount when the amount of diclofenac accumulated in the control composition is assumed to be 1.

[15] The aqueous composition according to any one of the above [10] to [14], which is for use in a treatment of a joint disease.

[16] The aqueous composition according to any one of the above [10] to [15], which contains the compound represented by the formula (1) at a concentration of 0.01 w/v % or more and 80 w/v % or less, 0.1 w/v % or more and 10 w/v % or less, 0.5 w/v % or more and 5 w/v % or less, or 1 w/v %.

[17] The aqueous composition according to any one of the above [11] to [16], which contains the filterability improving agent at a concentration of 0.01 w/v % or more and 60 w/v % or less, 0.1 w/v % or more and 30 w/v % or less, 1 w/v % or more and 15 w/v % or less, or 2 w/v % or more and less than 10 w/v %.

[18] The aqueous composition according to any one of the above [10] to [17], which contains water at a concentration of 10 w/v % or more and 99.98 w/v % or less, 60 w/v % or more and 99.8 w/v % or less, 80 w/v % or more and 98.5 w/v % or less, or more than 89 w/v % and 97 w/v % or less.

[19] A kit, including an injector in which the aqueous composition according to any one of the above [10] to [18] is filled in a syringe barrel.

[20] A kit, including a vial containing the aqueous composition according to any one of the above [10] to [18], and an injector.

[21] A method for producing a pharmaceutical composition containing a compound represented by the formula (1), including a step of allowing the compound represented by the formula (1) and a filterability improving agent to coexist.

[22] A method for improving the filterability of a compound represented by the formula (1), including a step of allowing a filterability improving agent to coexist with the compound represented by the formula (1).

[23] A method for treating a human joint disease, including a step of administering the aqueous composition according to any one of the above [10] to [18] to a joint of a patient with a joint disease.

DESCRIPTION OF EMBODIMENTS

According to the present invention, a Dic-HA-containing pharmaceutical composition in which the accumulation amount of diclofenac lactam is suppressed is provided.

Hereinafter, modes for carrying out the present invention will be described with reference to examples.

One aspect of the present invention relates to a pharmaceutical composition, containing a compound represented by the following formula (1) and a component (A) that is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

[Chem. 1]

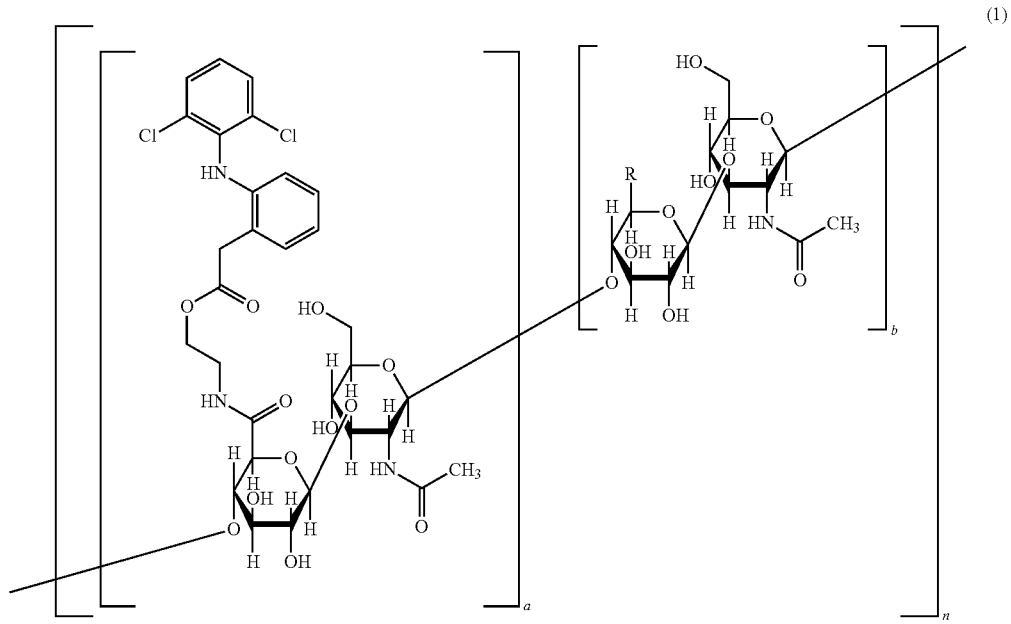

(wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit).

Another aspect of the present invention is a pharmaceutical composition, containing a compound represented by the formula (1) and an additional component, wherein the generation and/or accumulation of diclofenac is suppressed.

Another aspect of the present invention relates to a method for producing a pharmaceutical composition containing a compound represented by the formula (1), including a step of allowing the compound represented by the formula (1) and a component (A) that is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof to coexist.

Another aspect of the present invention relates to a method for suppressing the generation of diclofenac lactam from a compound represented by the formula (1), including a step of allowing at least one type selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof to coexist with the compound represented by the formula (1).

Still another aspect of the present invention relates to use of at least one type of substance selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof in the production of a pharmaceutical composition containing a compound represented by the formula (1), wherein the pharmaceutical composition is for use in a treatment of a joint disease, and the at least one type of substance is a compound that suppresses the generation of diclofenac lactam from the compound represented by the formula (1).

Still another aspect of the present invention relates to at least one type of compound for use in a treatment of a human joint disease, wherein the at least one type of compound is selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof, and is used as a constituent component of a pharmaceutical composition for treating a joint disease together with a compound represented by the formula (1).

Still another aspect of the present invention relates to a method for treating a human joint disease, including a step of administering a pharmaceutical composition to a joint of a patient with a joint disease, wherein the pharmaceutical composition is a pharmaceutical composition containing an effective amount of a compound represented by the formula (1) and at least one type of compound, and the at least one type of compound is selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof, and suppresses the generation of a diclofenac component from the compound represented by the formula (1).

Another aspect of the present invention relates to a method for storing a pharmaceutical composition, which is a method for storing a compound represented by the formula (1), wherein the pharmaceutical composition is a pharmaceutical composition in which the generation and/or accumulation of diclofenac lactam during storage is suppressed, and contains a compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof.

Still another aspect of the present invention relates to a kit including a pharmaceutical composition and an injector, wherein the pharmaceutical composition is a pharmaceutical composition containing a compound represented by the formula (1) and at least one type of compound, the at least one type of compound is selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof, and suppresses the generation of a diclofenac component from the compound represented by the formula (1).

According to one aspect of the present invention, in the pharmaceutical composition containing a compound represented by the formula (1), by allowing at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof to coexist, the accumulation of diclofenac lactam generated from the compound represented by the formula (1) during storage of the pharmaceutical composition can be suppressed.

According to one aspect of the present invention, in the pharmaceutical composition containing a compound represented by the formula (1), by allowing at least one type of compound selected from the group consisting of a nonionic surfactant, a hydroxyalkylated cyclodextrin, a $C_1$ to $C_3$ mono-alcohol, a $C_2$ to $C_3$ di-alcohol, a γ-lactone, polyvinylpyrrolidone, a chlorogenic acid, and an alkyl sulfate ester, and salts thereof to coexist, the accumulation of diclofenac generated from the compound represented by the formula (1) during storage of the pharmaceutical composition can be suppressed.

According to one aspect of the present invention, a pharmaceutical composition having excellent long-term stability and also having an extended shelf life is provided. The pharmaceutical composition can be stored in a container as an aqueous composition for injection (for example, a vial, a syringe barrel, or the like), and the accumulation of diclofenac lactam over time during a storage period is suppressed. Accordingly, the supply of the pharmaceutical composition is made efficient, and the cost for production, storage, or the like is reduced, and as a result, the pharmaceutical composition is a boon for patients who are users of the pharmaceutical composition.

In the present description, the "carboxylate salt group" is a structure in which a carboxylate [—C(=O)—O—] and a cation form a salt, and can be in the form of a pharmaceutically acceptable salt. The cation that forms a carboxylate salt is not particularly limited as long as it can form a salt with a carboxylate [—C(=O)—O—], but for example, a sodium ion, a potassium ion, a calcium ion, a magnesium ion, and the like can be exemplified. In a preferred embodiment, the carboxylate salt group is represented by —CO$_2$Na (that is, the cation is a sodium ion).

In the present description, as the "pharmaceutically acceptable salt", a metal salt such as a sodium salt, a potassium salt, a calcium salt, a magnesium salt, or a barium salt; an ammonium salt; an amine salt such as a methylamine salt, a diethylamine salt, an ethylenediamine salt, a cyclohexylamine salt, or an ethanolamine salt; an inorganic acid salt such as a hydrochloride salt, a sulfate salt, a hydrogen sulfate salt, a nitrate salt, a phosphate salt, a hydrobromide salt, or a hydroiodide salt; an organic acid salt such as an acetate salt, a phthalate salt, a fumarate salt, a maleate salt, an oxalate salt, a succinate salt, a methanesulfonate salt, a p-toluenesulfonate salt, a tartrate salt, a hydrogen tartrate salt, or a malate salt, or the like can be exemplified, but the salt is not limited thereto.

In the present description, the "diclofenac component" is used to refer to diclofenac and diclofenac lactam individually or collectively. The amount of the diclofenac component is measured by a method using high performance liquid chromatography (HPLC) described in Examples.

In the present description, the component (A) is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof. By containing the component (A), a pharmaceutical composition in which the generation and/or accumulation of diclofenac lactam is suppressed is provided.

In the present description, the phrase "allowed to coexist" means that target substances are put in a state where the substances can come into contact with each other. For example, it can be carried out by adding the component (A) to the compound represented by the formula (1), or by adding the compound represented by the formula (1) to the component (A). Further, it can also be carried out by mixing the compound represented by the formula (1) and the component (A).

The salt used as the component (A) is not particularly limited in the same manner as the above-mentioned "pharmaceutically acceptable salt", but for example, a pharmaceutically acceptable salt as described above or the like can be exemplified.

In an embodiment, the component (A) has, for example, a function of suppressing the accumulation and/or generation of diclofenac lactam in the composition containing the compound represented by the formula (1).

In a preferred embodiment, as the component (A), further a compound that suppresses the accumulation and/or generation of diclofenac in the composition containing the compound represented by the formula (1) is adopted.

In the present description, the "suppressing" the generation and accumulation of a diclofenac component means reducing the generation amount and/or accumulation amount of a diclofenac component.

The accumulation and/or generation of a diclofenac component can be determined by storing an aqueous composition in which the compound represented by the formula (1) and the component (A) are allowed to coexist in a thermostat bath at 60° C. for 1 week, and thereafter measuring the amount of a diclofenac component accumulated in the aqueous composition. An effect of suppressing the accumulation and/or an effect of suppressing the generation of a diclofenac component by the component (A) can be evaluated by calculating the amount of a diclofenac component in a test aqueous composition as a relative amount when an aqueous composition having the same formulation except that the component (A) is not contained is stored under the same conditions and the amount of a diclofenac component accumulated in the aqueous composition is assumed to be 1 as more specifically described in Examples (when the relative amount is smaller than 1, the accumulation and/or generation of a diclofenac component is suppressed). By this method, it is possible to determine whether or not the accumulation and/or generation of a diclofenac component is suppressed in the aqueous composition containing the compound represented by the formula (1).

The relative amount of diclofenac lactam calculated under the above conditions is preferably 0.9 or less, more preferably 0.8 or less, and further more preferably 0.75 or less. In addition, the relative amount of diclofenac calculated under the above conditions is preferably less than 1, more preferably 0.95 or less, and further more preferably 0.9 or less.

The composition may contain one type of component (A) alone or two or more types of components (A).

The combination of components (A) when two or more types are contained is also not particularly limited, but for example, a combination of two types of components (A): a polyalkylene glycol and a nonionic surfactant; a polyalkylene glycol and a hydroxyalkylated cyclodextrin; and the like, and a combination of three types of components (A): a polyalkylene glycol, a nonionic surfactant, and a hydroxyalkylated cyclodextrin are exemplified. As described in the below-mentioned Examples, by allowing a plurality of components (A) to coexist, a higher effect of suppressing a diclofenac component can be expected.

Further, another aspect of the present invention is an aqueous composition in which a compound represented by the formula (1) and a component that suppresses the accumulation and/or generation of a diclofenac component are allowed to coexist, wherein the relative amount of diclofenaclactam after storage in a thermostat bath at 60° C. for 1 week is 0.9 or less, and more preferably the relative amount is 0.75 or less. Note that the relative amount is a value when an aqueous composition (control composition) which is the same except that the component that suppresses the accumulation and/or generation of a diclofenac component is not contained is stored under the same conditions and the amount of diclofenaclactam accumulated in the control composition is assumed to be 1.

According to the study by the present inventors, it was revealed that the component (A) can also be utilized as an agent for suppressing the generation of a diclofenac component, an agent for suppressing the accumulation of diclofenac lactam in the composition, or an agent for improving the filterability of the aqueous composition containing a compound represented by the formula (1) as described below.

In an embodiment, the component (A) can be contained in the composition at a ratio of 0.01 w/v % or more and 60 w/v % or less, preferably 0.1 w/v % or more and 30 w/v % or less, more preferably 1 w/v % or more and 15 w/v % or less, and particularly preferably 2 w/v % or more and less than 10 w/v %.

Here, diclofenac has a structure represented by the following formula (2), and diclofenac lactam has a structure represented by the following formula (3).

[Chem. 2]

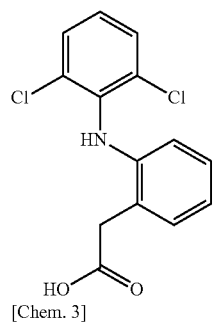

(2)

[Chem. 3]

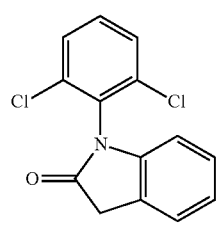

(3)

In the present description, the "nonionic surfactant" is intended to mean a nonionic surfactant that is commonly understood by those skilled in the art.

Non-limiting examples of the nonionic surfactant can include polysorbates (polysorbate 20, polysorbate 60, polysorbate 80, etc.), alkylphenol ethoxylates (octylphenol ethoxylate (Triton (trademark) X-100), nonylphenolethoxylate, etc.), alkyl glucosides (decyl glucoside, lauryl glucoside, octyl glucoside, etc.), polyoxyethylene glycol ethers (octaethylene glycol monododecyl ether, pentaethylene monododecyl ether, polyoxyethylene dodecyl ether, polyoxyethylene hexadecyl ether, etc.), polyoxyethylene glycol alkylphenol ethers (polyoxyethylene glycol octylphenol ether, polyoxyethylene glycol nonylphenol ether, etc.), polyoxyethylene lauryl ether, polyoxypropylene glycol alkyl ethers, glycerol alkyl esters, polyoxyethylene glycol sorbitan alkyl esters, monodecanoyl sucrose, cocamide, dodecyldimethylamine oxide, and alkoxylated alcohols (ethoxylated alcohols, propoxylated alcohols, ethoxylated propoxylated alcohols, etc.), and pharmaceutically acceptable salts thereof.

In an embodiment, polysorbate 20, polysorbate 80, Triton X-100, octyl glucoside, and pharmaceutically acceptable salts thereof are used as a preferred nonionic surfactant.

In the present description, the "hydroxyalkylated cyclodextrin" is intended to mean a hydroxyalkylated cyclodextrin that is commonly understood by those skilled in the art.

Non-limiting examples of the hydroxyalkylated cyclodextrin can include hydroxyethyl-β-cyclodextrin (HE-β-CD) and hydroxypropyl-β-cyclodextrin (HP-β-CD). In an embodiment, HE-β-CD and HP-β-CD are each used as a preferred hydroxyalkylated cyclodextrin.

In the present description, the "$C_1$ to $C_3$ mono-alcohol" means a mono-alcohol having 1 to 3 carbon atoms such as methanol, ethanol, n-propanol and isopropanol.

In an embodiment, ethanol is used as a preferred $C_1$ to $C_3$ mono-alcohol.

In the present description, the "$C_2$ to $C_3$ di-alcohol" means a di-alcohol having 2 to 3 carbon atoms such as 1,2-ethanediol and propylene glycol.

In an embodiment, propylene glycol is used as a preferred $C_2$ to $C_3$ di-alcohol.

In the present description, the "$C_3$ to $C_6$ tri-alcohol" means a tri-alcohol having 3 to 6 carbon atoms such as glycerin, 1,2,3-butanetriol and D-glucal.

In an embodiment, glycerin, 1,2,3-butanetriol and D-glucal are each used as a preferred $C_3$ to $C_6$ tri-alcohol.

In the present description, the "polyalkylene glycol" means a polymer of an alkylene glycol such as polyethylene glycol and polypropylene glycol. Non-limiting examples of the polyethylene glycol can include PEG 100 to 10000 (for example, PEG 200, PEG 300, PEG 400, PEG 500, PEG 600, PEG 4000, and PEG 6000). These examples are all used as a preferred polyalkylene glycol in an embodiment of the present invention.

In a preferred embodiment, polyethylene glycol having a weight average molecular weight of 200 or more and 6,000 or less is used.

In a more preferred embodiment, polyethylene glycol having a weight average molecular weight of 400 or more and 6,000 or less is used.

In the present description, the "γ-lactone" is intended to mean a lactone having a 5-membered ring that is commonly understood by those skilled in the art.

Non-limiting examples of the γ-lactone can include D-erythronolactone, sodium erythorbate, ascorbic acid, glucuronolactone, and pharmaceutically acceptable salts thereof.

In an embodiment, D-erythronolactone, sodium erythorbate, glucuronolactone, and pharmaceutically acceptable salts thereof are each used as a preferred γ-lactone.

In the present description, the "chlorogenic acid" means chlorogenic acid or an analogous compound thereof such as chlorogenic acid, ferroylquinic acid, dicaffeoylquinic acid, and a pharmaceutically acceptable salt thereof.

In an embodiment, chlorogenic acid and a pharmaceutically acceptable salt thereof are used as a preferred chlorogenic acid.

In the present description, the "alkyl sulfate ester" is intended to mean a sulfate ester having an octyl group, a nonyl group, a decyl group, a dodecyl group, or the like as an alkyl group, and a pharmaceutically acceptable salt thereof. As a representative alkyl sulfate ester, sodium dodecyl sulfate (SDS) can be exemplified.

In an embodiment, SDS is used as a preferred alkyl sulfate ester.

From the viewpoint of suppressing the generation and/or accumulation of diclofenac in the composition, in a preferred embodiment, as the component (A), at least one type of compound selected from the group consisting of a nonionic surfactant, a hydroxyalkylated cyclodextrin, a $C_1$ to $C_3$ mono-alcohol, a $C_2$ to $C_3$ di-alcohol, a γ-lactone, polyvinylpyrrolidone, a chlorogenic acid, and an alkyl sulfate ester, and salts thereof is used.

From the viewpoint of achieving excellent filter filterability of the composition, in a preferred embodiment, as the component (A), a compound selected from the group consisting of a polyalkylene glycol, a $C_1$ to $C_3$ mono-alcohol, and a hydroxyalkylated cyclodextrin, and salts thereof is used.

In the present invention, the pharmaceutical composition is preferably a composition to be used in a treatment of a human joint disease. In the present description, the "joint disease" is a disease in various joints such as a knee joint, a shoulder joint, a neck joint, a hip joint, a spine joint, a temporomandibular joint, a finger joint, an elbow joint, a hand joint, and a foot joint. As the joint disease, more specifically, osteoarthritis, rheumatoid arthritis, articular cartilage damage, osteonecrosis of a knee joint, osteonecrosis of a femur, shoulder arthritis, bacterial arthritis, viral arthritis, neuropathic arthrosis, and the like can be exemplified. The composition for use in a treatment of a joint disease according to the present invention is preferably used for osteoarthritis or rheumatoid arthritis, and is more preferably used for osteoarthritis.

In the present description, the "treatment" may be a treatment for a disease itself (for example, a treatment for healing or improving a structural disorder in a disease) or a treatment for various symptoms accompanying a disease (for example, a decrease in ADL caused by a joint such as pain, stiffness, or a joint function (that can be evaluated by, for example, difficulty in daily activities (represented by going up and down the stairs, getting in and out of the car, etc.))). Further, the "treatment" not only includes complete healing, but also includes improvement of some or all symptoms of a disease, and suppression of progression of a disease (including maintenance and reduction in progression rate) and prevention of a disease. Here, the prevention includes, for example, in a case where a structural disorder in a joint is observed, but various symptoms accompanying a joint disease such as joint functional disorder, pain, and/or stiffness do not occur, prevention of the onset of such symptoms. Further, the prevention includes, for example, in a case where a clear structural disorder in a joint is not observed, but various symptoms accompanying a joint disease such as joint functional disorder, pain, and/or stiffness have occurred, prevention of the onset of the structural disorder or suppression of the development of symptoms that are not manifested among the various symptoms. The composition is preferably used for improving, healing, or suppressing the progression of symptoms in a joint disease, and more preferably can be used for improving or healing symptoms. In an embodiment, the composition can be favorably used for improving, healing, or suppressing the progression of joint pain, or improving a joint function.

In the present description, the "effective amount" means a sufficient amount of a component for obtaining a desired response without having an excessive adverse effect (toxicity, irritation, an allergic reaction, etc.) corresponding to a rational risk/benefit ratio. The "effective amount" can vary depending on various factors such as the symptoms, body constitutions, age, and gender of a patient to whom the composition is administered. However, those skilled in the art can also determine the effective amount in other cases based on the results of one or a plurality of specific test examples and technical knowledge without requiring individual tests for respective combinations of various elements.

Hyaluronic acid includes a glycosaminoglycan constituted by a basic backbone, which has a structure composed of N-acetyl-D-glucosamine and D-glucuronic acid or a salt thereof that are linked via a β-(1,3) linkage as a disaccharide unit (hyaluronic acid constituent disaccharide unit), and in which the hyaluronic acid constituent disaccharide units are repeatedly linked via a β-(1,4) linkage, and is a glycosaminoglycan constituted by the basic backbone. Further, hyaluronic acid can be used even if it is obtained by any method such as a purified product derived from an animal or a microorganism or a synthesized product by chemical synthesis or the like.

The mass average molecular weight of each of hyaluronic acid and the compound represented by the formula (1) is not particularly limited, but is exemplified by 10,000 or more and 10,000,000 or less, and is preferably 500,000 or more and 5,000,000 or less, more preferably 600,000 or more and 3,000,000 or less, and further more preferably 600,000 or more and 1,200,000 or less. Note that in the present description, the "mass average molecular weight" of each of hyaluronic acid and the compound represented by the formula (1) is a value measured by an intrinsic viscosity method, and has the same meaning as the "weight average molecular weight" of each of these compounds.

Hyaluronic acid and the compound represented by the formula (1) may be in a state where a salt is not formed or in a state where a salt is formed. As such a salt, the pharmaceutically acceptable salt as described above can be exemplified.

The compound represented by the formula (1) can be obtained by covalently binding diclofenac to hyaluronic acid using 2-bromoethylamine hydrobromide, 2-aminoethanol or the like as a spacer compound.

In the compound represented by the formula (1), diclofenac and the spacer are linked through an ester bond, and the spacer and hyaluronic acid are linked through an amide bond.

Further, in the compound represented by the formula (1), the respective constituent disaccharide units can be linked in a random or block form at ratios a and b, respectively. That is, the diclofenac-introduced constituent disaccharide unit and the hyaluronic acid constituent disaccharide unit are bound to each other via a β-(1,4) linkage in a random or block form.

A terminal of the compound represented by the formula (1) is a hydrogen atom or a hydroxy group.

In the formula (1), a is the ratio of the number of diclofenac-introduced constituent disaccharide units to the number of all constituent disaccharide units, and b is the ratio of the number of hyaluronic acid constituent disaccharide units to the number of all constituent disaccharide units, and a+b is 1. In the formula (1), when the ratio represented by a is expressed by a molar fraction, the value of the molar fraction is referred to as "introduction ratio" in the present description. In the formula (1), a is 0.01 or more and 0.7 or less (as the introduction ratio, 1 mol % or more and 70 mol % or less, b is 0.3 or more and 0.99 or less), and preferably 0.1 or more and 0.2 or less (10 mol % or more and 20 mol % or less, b is 0.8 or more and 0.9 or less).

The value of a in the formula (1) or the introduction ratio can be adjusted by changing a condensing agent, a condensation aid, the reaction equivalent of a spacer compound, the reaction equivalent of diclofenac, or the like in a step of introduction reaction of diclofenac into hyaluronic acid.

Here, the "introduction ratio" in the present description is a value calculated according to the following calculation formula 1, and can be determined by measurement of an absorbance.

[Math. 3]

$$\text{Introduction ratio (mol \%)} = (\text{number of diclofenac-introduced constituent disaccharide units/number of all constituent disaccharide units}) \times 100 \quad \text{Calculation Formula 1:}$$

More specifically, the introduction ratio can be calculated according to the above formula using a previously created calibration curve of diclofenac by measuring an absorbance specific to diclofenac by a carbazole absorbance method.

In the compound represented by the formula (1), n represents the number of all constituent disaccharide units and can be calculated according to the following calculation formula 2 or 3.

When n is determined from the mass average molecular weight of hyaluronic acid that is a raw material, n can be calculated according to the following calculation formula 2.

[Math. 4]

$$n = (\text{mass average molecular weight of hyaluronic acid/mass average molecular weight of constituent disaccharide unit}) \quad \text{Calculation Formula 2:}$$

When n is determined from the mass average molecular weight of the compound represented by the formula (1) and a and b in the formula (1), n can be calculated according to the following calculation formula 3.

[Math. 5]

$$n = (\text{mass average molecular weight of compound represented by the formula (1)})/((\text{mass average molecular weight of diclofenac-introduced constituent disaccharide unit} \times a) + (\text{mass average molecular weight of hyaluronic acid constituent disaccharide unit} \times b)) \quad \text{Calculation Formula 3:}$$

n is an integer of 25 or more and 25,000 or less, preferably an integer of 1,250 or more and 12,500 or less, more preferably 1,500 or more and 7,500 or less, and further more preferably an integer of 1,500 or more and 3,000 or less.

As a method for introducing a spacer and diclofenac into hyaluronic acid, diclofenac may be introduced into hyaluronic acid into which a spacer has been introduced, or diclofenac into which a spacer has been introduced in advance may be reacted with hyaluronic acid. For example, those skilled in the art can appropriately carry out the method with reference to Patent Literature 1 or Patent Literature 2 or the like.

In an embodiment, the composition contains the compound represented by the formula (1) at a concentration of 0.01 w/v % or more and 80 w/v % or less. In a preferred embodiment, the compound represented by the formula (1) is contained at 0.1 w/v % or more and 10 w/v % or less, more preferably 0.5 w/v % or more and 5 w/v % or less, and particularly preferably 1 w/v %.

The composition can contain a pharmaceutically acceptable carrier in addition to the compound represented by the formula (1). As the pharmaceutically acceptable carrier, an aqueous medium such as water for injection, physiological saline, or Ringer's solution is preferably exemplified. In an embodiment, the pharmaceutical composition is an aqueous composition. In an embodiment, the composition is prepared by mixing the pharmaceutically acceptable carrier and the compound represented by the formula (1). According to need, an additive such as a buffer may be added to the composition. In addition, the composition may be subjected to a treatment such as dust removal, bacteria removal, or sterilization by, for example, filter filtration or the like after mixing the respective components.

In general, when the composition such as the pharmaceutical composition is applied to a living organism (a mammal, particularly a human is preferred), dust removal and sterilization are needed. In the case of the aqueous composition, from the viewpoint of stability of components or simplicity, it is preferred to perform a dust removal and sterilization step by filtration. When the composition is subjected to a sterilization treatment or the like by filter filtration, a commercially available membrane filter, sterilized container, sterilized injector, syringe barrel, or the like can be used as appropriate. For example, as a membrane filter, a membrane filter with a pore size of 0.22 μm can be used. Since the aqueous composition containing the compound represented by the formula (1) has high viscosity, it may cause difficulty in preparation of the aqueous composition, particularly in filter sterilization due to low filterability in some embodiments.

Here, the aqueous composition containing the compound represented by the formula (1) has low filterability. Patent Literature 1 indicates that by subjecting a solution containing Dic-HA to an alkali treatment, a transparent solution having permeability through a filtration filter can be formed. However, when the present inventors advanced the study, it was found that when an aqueous composition containing Dic-HA is subjected to an alkali treatment, the generation of a diclofenac component proceeds. On the other hand, it was found that when the sterilization of the aqueous composition containing the compound represented by the formula (1) is performed by heating sterilization instead of filter sterilization, the generation of a diclofenac component proceeds after all.

A certain aspect of the present invention relates to an aqueous composition containing the compound represented by the formula (1) and showing a maximum treatment amount ($V_{max}$) of 1.0 g/cm² or more in the following calculation method. According to such an aqueous composition, filter filtration can be performed, and therefore, the generation of a diclofenac component in the dust removal and sterilization step can be prevented/suppressed.

The calculation of the maximum treatment amount ($V_{max}$) is more specifically performed as follows. That is, the aqueous composition at a liquid temperature of 70° C. is filtered under a pressure of 0.6 MPa using a polyvinylidene fluoride filtration membrane with a pore size of 0.22 μm. At that time, the total filtration amount per effective filtration area (V) of the filtration membrane is measured every 30 seconds until the flow rate (Q) becomes 1/10 or less of the flow rate at the start of filtration. By plotting the measurement results with the filtration time (t) along the horizontal axis and t/V along the vertical axis, the following formula A is calculated within a range of the measurement point where the transition of t/V is stable. The maximum treatment amount ($V_{max}$) is determined from the reciprocal of the slope a of the calculation formula A (that is, the following calculation formula B). Note that the flow rate (Q) is the filtration amount per unit time (that is, Q=dV/dt).

Calculation Formula A: $t/V = at + b$ [Math. 1]

Calculation Formula B: $V_{max} = 1/a$ [Math. 2]

In the above calculation formulae A and B, t represents the filtration time (min), V represents the total filtration amount per effective filtration area (g/cm²), a is the slope of the calculation formula A, and b is the intercept of the calculation formula A.

As the maximum treatment amount ($V_{max}$) is larger (that is, as the filter filterability is higher), the filter is less likely to be clogged, and the time required for filtration is reduced.

Note that the $V_{max}$ itself is an evaluation index used in the selection or optimization of the filtration filter (if necessary, see "Vmax Test, Filter Selection and Optimization Methods", written by Kimihiko Kobayashi, Bioprocess Technical Sheet, Basic Technique No. 2, Japan Millipore, August, 1997).

The aqueous composition containing the compound represented by the formula (1) and showing a maximum treatment amount ($V_{max}$) of 1.0 g/cm² or more is useful as a pharmaceutical composition or an intermediate thereof. The maximum treatment amount ($V_{max}$) is preferably 6.0 g/cm² or more, more preferably 8.0 g/cm² or more, further more preferably 10 g/cm² or more, still further more preferably 15 g/cm² or more, and particularly preferably 20 g/cm² or more. The upper limit of the maximum treatment amount ($V_{max}$) is not particularly limited, but is, for example, 2000 g/cm² or less (1500 g/cm² or less, 1200 g/cm² or less, 1000 g/cm² or less, 800 g/cm² or less, 500 g/cm² or less, or 200 g/cm² or less). The $V_{max}$ may be, for example, 1.0 g/cm² or more and 2000 g/cm² or less, 6.0 g/cm² or more and 1500 g/cm² or less, 8.0 g/cm² or more and 1000 g/cm² or less, 10 g/cm² or more and 800 g/cm² or less, 15 g/cm² or more and 500 g/cm² or less, or 15 g/cm² or more and 200 g/cm² or less.

In an embodiment, the aqueous composition further contains a filterability improving agent. In the present invention, the "filterability improving agent" is not particularly limited as long as it improves the filterability, that is, the maximum treatment amount ($V_{max}$) of the aqueous composition containing the compound represented by the formula (1). As a specific example of the filterability improving agent, for example, the above-mentioned component (A) can be exemplified, but it is not limited thereto.

In an embodiment, the filterability improving agent is selected from the group consisting of a polyalkylene glycol, a $C_1$ to $C_3$ mono-alcohol, and a hydroxyalkylated cyclodextrin as described above.

From the viewpoint of filterability, in a preferred embodiment, PEG 200 to 6000, methanol, ethanol, n-propanol, isopropanol, hydroxyethyl-β-cyclodextrin, and hydroxypropyl-β-cyclodextrin are used as the filterability improving agent.

In a more preferred embodiment, a compound selected from the group consisting of PEG 400, PEG 4000, ethanol, and hydroxypropyl-β-cyclodextrin can be used in the composition as the filterability improving agent.

As an embodiment, when PEG 400 is contained, the filterability is remarkably improved, and therefore, it can be particularly preferably used as the filterability improving agent.

The aqueous composition may contain one type of filterability improving agent alone or two or more types of filterability improving agents.

In an embodiment, in the aqueous composition, the filterability improving agent can be contained at a ratio of 0.01 w/v % or more and 60 w/v % or less, preferably 0.1 w/v % or more and 30 w/v % or less, more preferably 1 w/v % or more and 15 w/v % or less, and particularly preferably 2 w/v % or more and less than 10 w/v %.

In the present description, the "aqueous composition" is a composition containing water at 10 w/v % or more and 99.98 w/v % or less. The aqueous composition may be in the form of a solution, a suspension, or a gel. As water to be used in the preparation of the aqueous composition, for example, water for injection, purified water, distilled water, and the like can be exemplified. The content of water in the aqueous composition is preferably 60 w/v % or more and 99.8 w/v % or less, more preferably 80 w/v % or more and 98.5 w/v % or less, and particularly preferably more than 89 w/v % and 97 w/v % or less.

In an embodiment, the maximum treatment amount ($V_{max}$) of the aqueous composition containing the compound represented by the formula (1) is 1.0 g/cm² or more, and the relative amount of diclofenac lactam is 0.9 or less. In a preferred embodiment, the maximum treatment amount ($V_{max}$) of the aqueous composition containing the compound represented by the formula (1) is 6.0 g/cm² or more, and the relative amount of diclofenac lactam is 0.8 or less. In a more preferred embodiment, the maximum treatment amount ($V_m$ax) of the aqueous composition containing the compound represented by the formula (1) is 8.0 g/cm² or more, and the relative amount of diclofenac lactam is 0.75 or less. Note that the relative amount of diclofenac lactam is obtained by storing a test composition in which the compound represented by the formula (1) and the filterability improving agent are allowed to coexist, and a control composition having the same formulation as the test composition except that the filterability improving agent is not contained for 1 week in a thermostat bath at 60° C., and thereafter measuring the amount of diclofenac lactam accumulated in the test composition and the control composition by high performance liquid chromatography, and calculating the relative amount when the amount of diclofenac lactam accumulated in the control composition is assumed to be 1.

As the buffer that can be contained in the composition, a buffer well known to those skilled in the art can be used as appropriate. As a non-limiting example, utilization of a citrate buffer solution, an acetate buffer solution, or a phosphate buffer solution as the buffer is exemplified.

In an embodiment, as the citrate buffer solution, a solution containing a final concentration of 0.1 mM to 500 mM (for example, 1 mM to 50 mM) as citric acid is exemplified. Here, the citrate buffer solution is preferably a citrate buffer solution adjusted to pH 4.5 to 5.5. As an example of the pH of a more preferred citrate buffer solution, pH 4.8 to pH 5.4, and further as one example thereof, pH 5.1 can be exemplified.

In an embodiment, as the acetate buffer solution, a solution containing a final concentration of 0.1 mM to 500 mM (for example, 1 mM to 50 mM) as acetic acid is exemplified. Here, the acetate buffer solution is preferably an acetate buffer solution adjusted to pH 4.5 to 5.5. As an example of the pH of a more preferred acetate buffer solution, pH 4.8 to pH 5.4, and further as one example thereof, pH 5.1 can be exemplified.

In an embodiment, as the phosphate buffer solution, a solution containing a final concentration of 0.1 mM to 500 mM (for example, 1 mM to 50 mM) as phosphoric acid is exemplified. Here, the phosphate buffer solution is preferably a phosphate buffer solution adjusted to pH 6.0 to 7.0. As an example of the pH of a more preferred phosphate buffer solution, pH 6.3 to pH 6.8, and further as one example thereof, pH 6.5 can be exemplified.

In an embodiment, the citrate buffer solution is used in combination with one or two or more selected from the group consisting of a $C_3$ to $C_6$ tri-alcohol, a polyalkylene glycol, an alkyl sulfate ester, a nonionic surfactant, a $C_1$ to $C_3$ mono-alcohol, a γ-lactone, a chlorogenic acid, a $C_2$ to $C_3$ di-alcohol, and polyvinylpyrrolidone, and salts thereof as the component (A).

In an embodiment, the acetate buffer solution is used in combination with one or two or more selected from the group consisting of a hydroxyalkylated cyclodextrin, a polyalkylene glycol, a $C_1$ to $C_3$ mono-alcohol, a nonionic surfactant, and polyvinylpyrrolidone, and salts thereof as the component (A).

In an embodiment, the phosphate buffer solution is used in combination with one or two or more selected from the group consisting of a γ-lactone, a polyalkylene glycol, and a $C_3$ to $C_6$ tri-alcohol, and salts thereof as the component (A).

In an embodiment, the composition is prepared by a procedure as described below.

(Step 1) Predetermined amounts of citric acid hydrate, disodium citrate hydrate, and PEG 400 are dissolved in water for injection (WFI).

(Step 2) A predetermined amount of the compound represented by the formula (1) (introduction ratio: 18 mol %) is dissolved in the solution of Step 1. Then, the solution after dissolution is heated to 70° C. and degassed by heating under reduced pressure.

(Step 3) The solution of Step 2 is sterilized by filtration through a filter with a pore size of 0.22 μm.

(Step 4) The solution of Step 3 is degassed by heating at 70° C., and then cooled to 10° C.

(Step 5) A predetermined amount is filled in a syringe under sterilization conditions.

By the above (Step 1) to (Step 5), a sterilized pharmaceutical composition containing a hyaluronic acid derivative, PEG 400, and a citrate buffer solution is prepared. Here, as the concentrations of the respective components, the hyaluronic acid derivative: 0.5 to 5 w/v %, PEG 400: 3 to 30 w/v %, and the phosphate buffer solution: 3 to 30 mM (in terms of citric acid) are exemplified, however, the concentrations of the various components in the pharmaceutical composition are not limited to the above respective ranges. It goes without saying that the component (A) is not limited to PEG 400, and also the buffer solution is not limited to citrate buffer solution. The same applies to the configuration of the hyaluronic acid derivative and the pore size of the membrane filter.

When the maximum treatment amount ($V_{max}$) of the aqueous composition is 1.0 g/cm² or more, the suitability for filter sterilization with a filter is enhanced, and therefore, the generation of diclofenac lactam in the sterilization step can be suppressed.

The sterilized pharmaceutical composition after preparation can be stored at a low temperature such as 4° C., or at normal temperature. In order to suppress the decomposition of the hyaluronic acid derivative, it is more desirable to store the composition at a low temperature such as 4° C. For example, in a case where the accumulation amount of diclofenac lactam of 0.5 w/w % with respect to the amount of the hyaluronic acid derivative in the pharmaceutical composition is set as a threshold value, and when the accumulation amount exceeds the threshold value, the quality as a pharmaceutical product is determined to be unqualified, if the solution is a favorable formulation, the composition can be stored for about several months to 1 year even in an environment at normal temperature (25° C.) while keeping the qualified quality. The storage period can be extended by about 1 month to over 3 months by allowing the component (A) to coexist by conversion based on the results of the storage test in Examples described below (The conversion was performed on the premise that the accumulation of diclofenac lactam is suppressed by 10 to 25% by the coexistence of the component (A). The suppression ratio is a sufficiently achievable level from, for example, the below-mentioned Example 1 (the results in (1-2) or the like). If the storage life of the pharmaceutical composition whose storage life with the qualified quality is several months can be extended by 1 to 3 months, it is obvious that this leads to cost reduction, and the burden on patients is reduced, and also contribution to health economics is achieved. Further, the sterilized pharmaceutical composition after preparation is more preferably stored under light-shielding conditions. As such conditions, storage in a refrigerator or the like while keeping the sterilized pharmaceutical composition packaged is exemplified.

The frequency of administration of the pharmaceutical composition is appropriately adjusted according to the symptoms of a patient, or the like. From the viewpoint of drug efficacy, for example, a frequency of once a week to once every 52 weeks can be exemplified. As a more preferred example, a frequency of once every 2 weeks to once every 26 weeks, or once every 4 weeks to once every 13 weeks is exemplified. When sufficient remission is obtained by a single administration, of course, only a single administration may be adopted. A preferred preparation mode of the composition is a solution for an injection (for example, an aqueous composition). For example, when the composition is administered as an injection to an affected area such as a knee joint, it is desirable that the administration interval is long in consideration of the physical burden or mental burden on the patient. In particular, when the composition is used as an injection, the solution properties thereof are preferably colorless and clear.

In an embodiment, an injector in which the pharmaceutical composition according to the present invention is filled in a syringe barrel is provided. In an embodiment, a kit including an injector in which the pharmaceutical composition according to the present invention is filled in a syringe barrel can also be provided. The injector includes a plunger for drug extrusion, or the like, and is capable of extruding the composition according to the present invention. In an embodiment, the composition filled in the injector can be provided in a sterile state. In an embodiment, a single dose of the composition is filled in the syringe barrel in advance.

In addition, the kit can be formed into a kit including a medicinal injection prepared by filling a solution in which the compound represented by the formula (1) is dissolved in a citrate buffer solution, an acetate buffer solution, a phosphate buffer solution, physiological saline, or water for injection in a syringe barrel, and sealing the syringe barrel slidably with a plunger for drug extrusion. Here, the osmotic pressure or viscosity of the solution can be appropriately adjusted as needed. As the plunger for drug extrusion, a commonly used one can be used, but it is formed of an elastic body such as rubber or synthetic rubber, and is slidably inserted into the syringe barrel in a close contact state. Further, the kit may include a plunger rod for extruding the drug by performing an operation of pushing in the plunger, or an instruction manual or a package insert, or the like. Further, in an embodiment, the pharmaceutical composition according to the present invention is provided by being stored in a vial bottle instead of being filled in a syringe barrel as described above. In that case, the vial bottle may sometimes be provided together with an injector containing a sterilized empty syringe barrel. In addition, it can also be provided as a kit including the vial bottle and the injector.

As apparent to those skilled in the art, the preferred features and characteristics of one aspect of the present invention may be independent of each other or can also be applied in combination with another aspect of the present invention.

In an embodiment, a pharmaceutical composition in which the generation and/or accumulation of diclofenac lactam is suppressed and the generation and/or accumulation of diclofenac is suppressed, and a method for producing the same are provided.

In an embodiment, an aqueous composition, which shows a maximum treatment amount ($V_{max}$) of 1.0 g/cm² or more, and in which the generation of diclofenac lactam is suppressed, and a method for producing the same are provided.

In an embodiment, an aqueous composition, which shows a maximum treatment amount ($V_{max}$) of 1.0 g/cm² or more, and in which the generation of diclofenac is suppressed, and a method for producing the same are provided.

In an embodiment, an aqueous composition, which shows a maximum treatment amount ($V_{max}$) of 1.0 g/cm² or more, and in which the generation of diclofenac lactam and the generation of diclofenac are suppressed, and a method for producing the same are provided.

In a specific embodiment, a pharmaceutical composition, which contains a compound represented by the formula (1) and at least one type of compound selected from the group consisting of a nonionic surfactant, a hydroxyalkylated cyclodextrin, a $C_1$ to $C_3$ mono-alcohol, a $C_2$ to $C_3$ di-alcohol, a γ-lactone, polyvinylpyrrolidone, a chlorogenic acid, and an alkyl sulfate ester, and salts thereof, and in which the generation and/or accumulation of diclofenac lactam is suppressed and the generation and/or accumulation of diclofenac is suppressed, is provided.

In a specific embodiment, a pharmaceutical composition, which contains a compound represented by the formula (1) and at least one type of compound selected from the group consisting of a polyalkylene glycol, a $C_1$ to $C_3$ mono-alcohol, and a hydroxyalkylated cyclodextrin, and salts thereof, in which the generation of diclofenac lactam is suppressed, and which shows a maximum treatment amount ($V_{max}$) of 1.0 g/cm² or more, and has improved filterability, is provided.

In a specific embodiment, a pharmaceutical composition, which contains a compound represented by the formula (1)

and at least one type of compound selected from the group consisting of a $C_1$ to $C_3$ mono-alcohol, and a hydroxyalkylated cyclodextrin, and salts thereof, in which the generation of diclofenac is suppressed, and which shows a maximum treatment amount ($V_{max}$) of 1.0 g/cm² or more, and has improved filterability, is provided.

In a specific embodiment, a pharmaceutical composition, which contains a compound represented by the formula (1) and at least one type of compound selected from the group consisting of a $C_1$ to $C_3$ mono-alcohol, and a hydroxyalkylated cyclodextrin, and salts thereof, in which the generation of diclofenac lactam and the generation of diclofenac are suppressed, and which shows a maximum treatment amount ($V_{max}$) of 1.0 g/cm² or more, and has improved filterability, is provided.

In a specific embodiment, a method for suppressing the generation of diclofenac lactam and the generation of diclofenac from a compound represented by the formula (1), including a step of allowing the compound represented by the formula (1) and at least one type of compound selected from the group consisting of a nonionic surfactant, a hydroxyalkylated cyclodextrin, a $C_1$ to $C_3$ mono-alcohol, a $C_2$ to $C_3$ di-alcohol, a γ-lactone, polyvinylpyrrolidone, a chlorogenic acid, and an alkyl sulfate ester, and salts thereof to coexist is provided.

In a specific embodiment, a method for suppressing the generation of diclofenac lactam from a compound represented by the formula (1) and improving the filterability of the compound represented by the formula (1), including a step of allowing the compound represented by the formula (1) and at least one type of compound selected from the group consisting of a polyalkylene glycol, a $C_1$ to $C_3$ mono-alcohol, and a hydroxyalkylated cyclodextrin, and salts thereof to coexist is provided.

In a specific embodiment, a method for suppressing the generation of diclofenac from a compound represented by the formula (1) and improving the filterability of the compound represented by the formula (1), including a step of allowing the compound represented by the formula (1) and at least one type of compound selected from the group consisting of a $C_1$ to $C_3$ mono-alcohol, and a hydroxyalkylated cyclodextrin, and salts thereof to coexist is provided.

In a specific embodiment, a method for suppressing the generation of diclofenac lactam and the generation of diclofenac from a compound represented by the formula (1) and improving the filterability of the compound represented by the formula (1), including a step of allowing the compound represented by the formula (1) and at least one type of compound selected from the group consisting of a $C_1$ to $C_3$ mono-alcohol, and a hydroxyalkylated cyclodextrin, and salts thereof to coexist is provided.

EMBODIMENTS

Preferred embodiments of the present invention will be exemplified below.

[1] A pharmaceutical composition, containing a compound represented by the formula (1) and a component (A):

the component (A): at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

[Chem. 1]

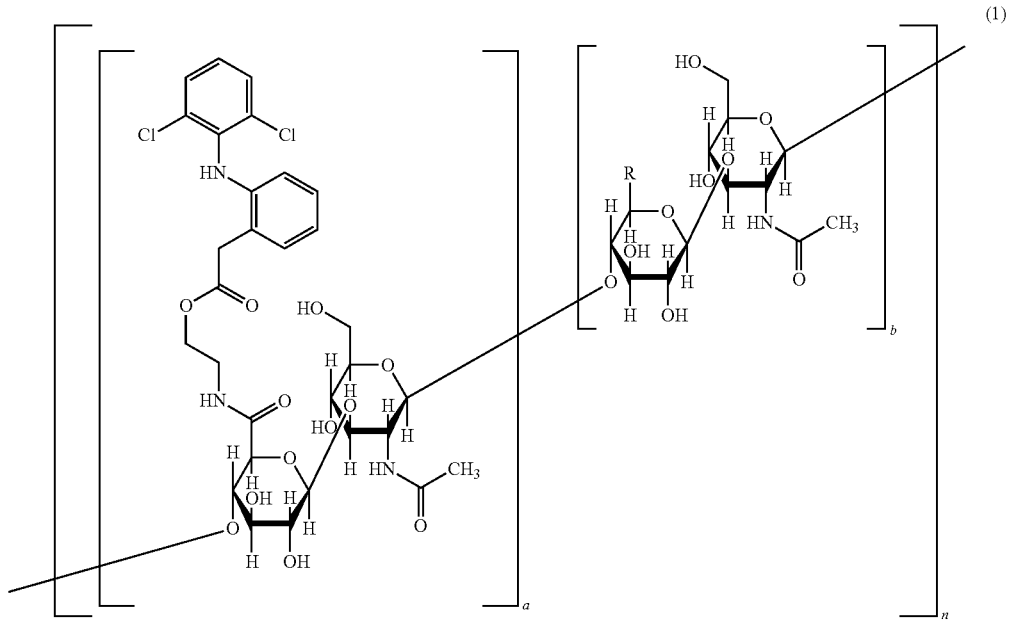

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[2] The pharmaceutical composition according to the above [1], wherein the component (A) is selected from the group consisting of a nonionic surfactant, a hydroxyalkylated cyclodextrin, a $C_1$ to $C_3$ mono-alcohol, and a polyalkylene glycol.

[3] The pharmaceutical composition according to the above [1] or [2], wherein the polyalkylene glycol is polyethylene glycol.

[4] The pharmaceutical composition according to the above [3], wherein the weight average molecular weight of polyethylene glycol is 200 or more and 6,000 or less.

[5] The pharmaceutical composition according to any one of the above [1] to [4], which contains the compound represented by the formula (1) at a concentration of 0.01 w/v % or more and 80 w/v % or less, 0.1 w/v % or more and 10 w/v % or less, 0.5 w/v % or more and 5 w/v % or less, or 1 w/v %.

[6] The pharmaceutical composition according to any one of the above [1] to [5], wherein the final concentration of the component (A) is 0.01 w/v % or more and 60 w/v % or less, 0.01 w/v % or more and 30 w/v % or less, 1 w/v % or more and 15 w/v % or less, or 2 w/v % or more and less than 10 w/v %.

[7] The pharmaceutical composition according to any one of the above [1] to [6], further containing a buffer solution selected from the group consisting of a phosphate buffer solution, a citrate buffer solution, and an acetate buffer solution.

[8] The pharmaceutical composition according to any one of the above [1] to [7], wherein the pH is from 4.5 to 7.0.

[9] The pharmaceutical composition according to any one of the above [1] to [8], which is an aqueous composition.

[10] The pharmaceutical composition according to any one of the above [1] to [9], which is a pharmaceutical composition for treating a joint disease.

[11] The pharmaceutical composition according to the above [10], wherein the joint disease is osteoarthritis or rheumatoid arthritis.

[12] A kit, including an injector in which the pharmaceutical composition according to any one of the above [1] to [11] is filled in a syringe barrel.

[13] A kit, including a vial containing the pharmaceutical composition according to any one of the above [1] to [11], and an injector.

[14] A method for producing a pharmaceutical composition containing a compound represented by the following formula (1), including a step of allowing the compound represented by the following formula (1) and a component (A) to coexist:

the component (A): at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

[Chem. 1]

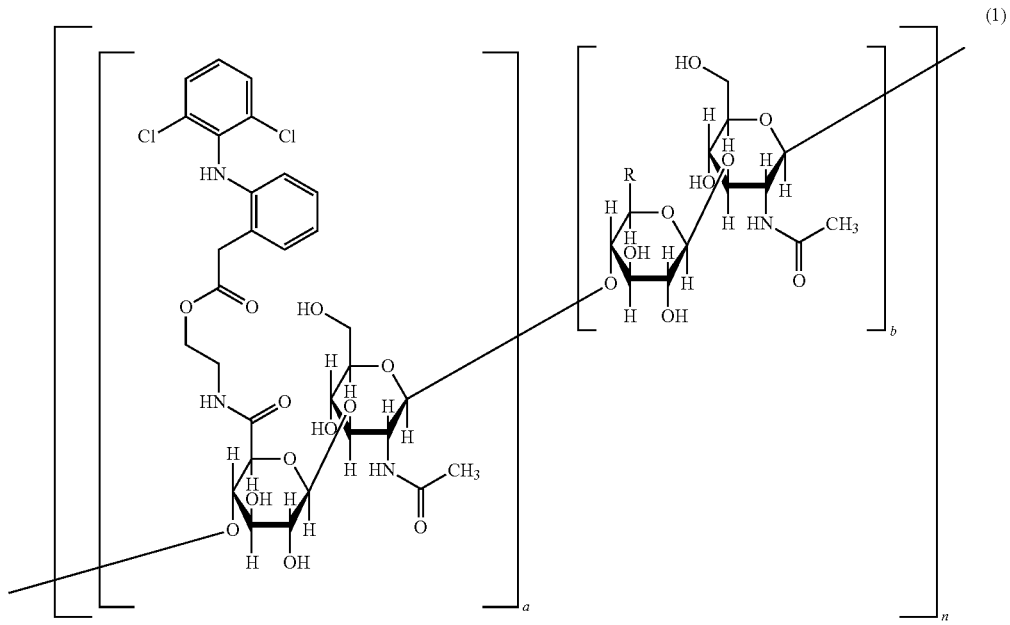

(1)

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[15] The method according to the above [14], wherein the component (A) is selected from the group consisting of a nonionic surfactant, a hydroxyalkylated cyclodextrin, a $C_1$ to $C_3$ mono-alcohol, and a polyalkylene glycol.

[16] The method according to the above [14] or [15], wherein the polyalkylene glycol is polyethylene glycol.

[17] The method according to the above [16], wherein the weight average molecular weight of polyethylene glycol is 200 or more and 6,000 or less.

[18] The method according to any one of the above [14] to [17], wherein the compound represented by the formula (1) is added at a final concentration of 0.01 w/v % or more and 80 w/v % or less, 0.1 w/v % or more and 10 w/v % or less, 0.5 w/v % or more and 5 w/v % or less, or 1 w/v %.

[19] The method according to any one of the above [14] to [18], wherein the component (A) is added at a final concentration of 0.01 w/v % or more and 60 w/v % or less, 0.01 w/v % or more and 30 w/v % or less, 1 w/v % or more and 15 w/v % or less, or 2 w/v % or more and less than 10 w/v %.

[20] The method according to any one of the above [14] to [19], wherein the compound represented by the formula (1) and/or the component (A) contains a buffer solution selected from the group consisting of a phosphate buffer solution, a citrate buffer solution, and an acetate buffer solution.

[21] The method according to any one of the above [14] to [20], wherein the pH of the pharmaceutical composition is from 4.5 to 7.0.

[22] The method according to any one of the above [14] to [21], wherein the pharmaceutical composition is an aqueous composition.

[23] A method for suppressing the generation of diclofenac lactam from a compound represented by the following formula (1), including a step of allowing a component (A) to coexist with the compound represented by the following formula (1):

the component (A): at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

[24] The method according to the above [23], wherein the component (A) is selected from the group consisting of a nonionic surfactant, a hydroxyalkylated cyclodextrin, a $C_1$ to $C_3$ mono-alcohol, and a polyalkylene glycol.

[25] The method according to the above [23] or [24], wherein the polyalkylene glycol is polyethylene glycol.

[26] The method according to the above [25], wherein the weight average molecular weight of polyethylene glycol is 200 or more and 6,000 or less.

[27] The method according to any one of the above [23] to [26], wherein the component (A) is added at a final concentration of 0.01 w/v % or more and 60 w/v % or less, 0.01 w/v % or more and 30 w/v % or less, 1 w/v % or more and 15 w/v % or less, or 2 w/v % or more and less than 10 w/v %.

[28] The method according to any one of the above [23] to [27], wherein the compound represented by the formula (1) and/or the component (A) contains a buffer solution selected from the group consisting of a phosphate buffer solution, a citrate buffer solution, and an acetate buffer solution.

[29] The method according to any one of the above [23] to [28], which is performed at a pH in a range of 4.5 to 7.0.

[30] The method according to any one of the above [23] to [29], wherein the compound represented by the formula (1) and the component (A) are allowed to coexist in an aqueous solvent.

[31] A method for suppressing the accumulation of diclofenac lactam in a pharmaceutical composition containing a compound represented by the following formula (1), including a step of allowing the compound represented by the formula (1) and a component (A) to coexist:

the component (A): at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

[Chem. 1]

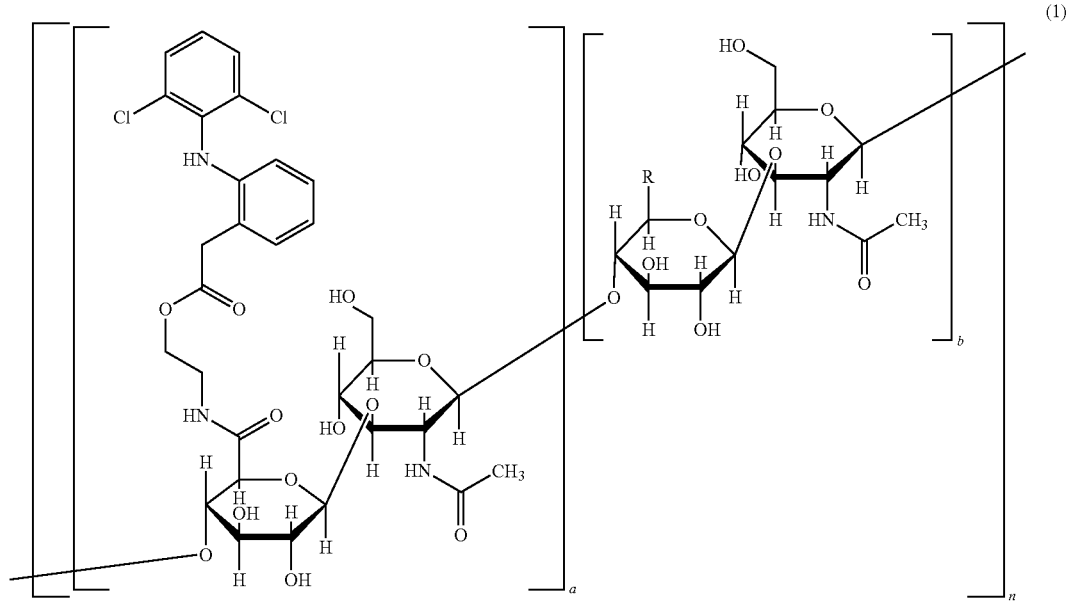

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[Chem. 1]

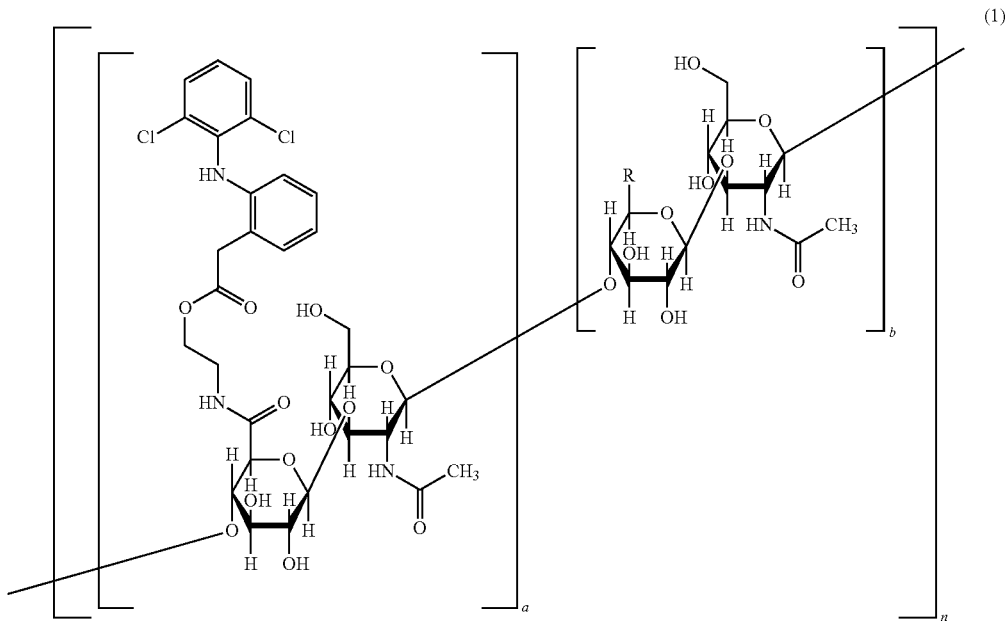

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[32] The method according to the above [31], wherein the component (A) is selected from the group consisting of a nonionic surfactant, a hydroxyalkylated cyclodextrin, a $C_1$ to $C_3$ mono-alcohol, and a polyalkylene glycol.

[33] The method according to the above [31] or [32], wherein the polyalkylene glycol is polyethylene glycol.

[34] The method according to the above [33], wherein the weight average molecular weight of polyethylene glycol is 200 or more and 6,000 or less.

[35] The method according to any one of the above [31] to [34], wherein the pharmaceutical composition contains the compound represented by the formula (1) at a concentration of 0.01 w/v % or more and 80 w/v % or less, 0.1 w/v % or more and 10 w/v % or less, 0.5 w/v % or more and 5 w/v % or less, or 1 w/v %.

[36] The method according to any one of the above [31] to [35], wherein the component (A) is added at a final concentration of 0.01 w/v % or more and 60 w/v % or less, 0.01 w/v % or more and 30 w/v % or less, 1 w/v % or more and 15 w/v % or less, or 2 w/v % or more and less than 10 w/v %.

[37] The method according to any one of the above [31] to [36], wherein the compound represented by the formula (1) and/or the component (A) contains a buffer solution selected from the group consisting of a phosphate buffer solution, a citrate buffer solution, and an acetate buffer solution.

[38] The method according to any one of the above [31] to [37], which is performed at a pH in a range of 4.5 to 7.0.

[39] The method according to any one of the above [31] to [38], wherein the pharmaceutical composition is an aqueous composition.

[40] The method according to any one of the above [31] to [39], wherein the pharmaceutical composition is a pharmaceutical composition for treating a joint disease.

[41] The pharmaceutical composition according to the above [40], wherein the joint disease is osteoarthritis or rheumatoid arthritis.

[42] Use of a component (A) in the production of a pharmaceutical composition containing a compound represented by the following formula (1), wherein the component (A) is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof, and the production includes a step of allowing the component (A) and the compound represented by the formula (1) to coexist:

[Chem. 1]

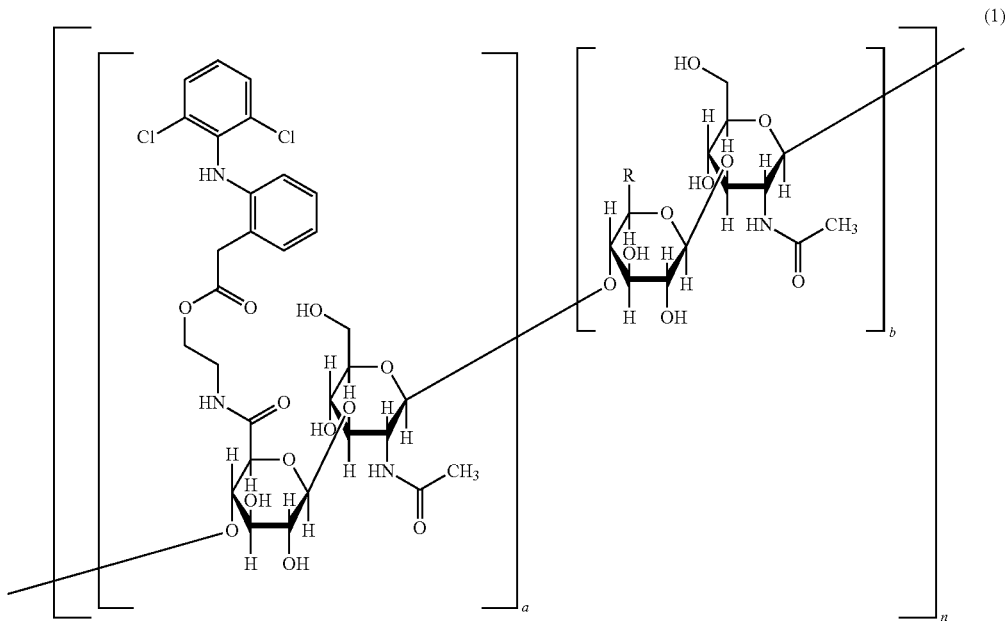

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[43] The use according to the above [42], wherein the component (A) is selected from the group consisting of a nonionic surfactant, a hydroxyalkylated cyclodextrin, a $C_1$ to $C_3$ mono-alcohol, and a polyalkylene glycol.

[44] The use according to the above [42] or [43], wherein the polyalkylene glycol is polyethylene glycol.

[45] The use according to the above [44], wherein the weight average molecular weight of polyethylene glycol is 200 or more and 6,000 or less.

[46] The use according to any one of the above [42] to [45], wherein the pharmaceutical composition contains the compound represented by the formula (1) at a concentration of 0.01 w/v % or more and 80 w/v % or less, 0.1 w/v % or more and 10 w/v % or less, 0.5 w/v % or more and 5 w/v % or less, or 1 w/v %.

[47] The use according to any one of the above [42] to [46], wherein the component (A) is added at a final concentration of 0.01 w/v % or more and 60 w/v % or less, 0.01 w/v % or more and 30 w/v % or less, 1 w/v % or more and 15 w/v % or less, or 2 w/v % or more and less than 10 w/v %.

[48] The use according to any one of the above [42] to [47], wherein the pharmaceutical composition is a pharmaceutical composition for treating a joint disease.

[49] The use according to the above [48], wherein the joint disease is osteoarthritis or rheumatoid arthritis.

[50] A component (A), which is for use in a treatment of a human joint disease, wherein the component (A) is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof, and in the treatment, the component (A) and a compound represented by the following formula (1) are both used as constituent components of a pharmaceutical composition for treating a joint disease:

[Chem. 1]

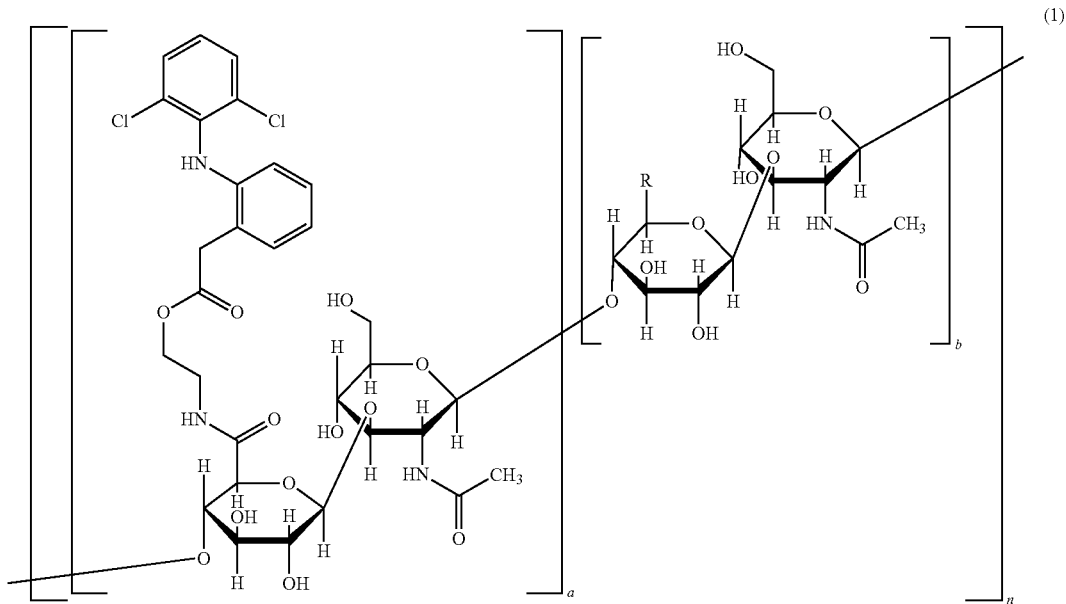

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[51] The component (A) according to the above [50], wherein the component (A) is selected from the group consisting of a nonionic surfactant, a hydroxyalkylated cyclodextrin, a $C_1$ to $C_3$ mono-alcohol, and a polyalkylene glycol.

[52] The component (A) according to the above [50] or [51], wherein the polyalkylene glycol is polyethylene glycol.

[53] The component (A) according to the above [52], wherein the weight average molecular weight of polyethylene glycol is 200 or more and 6,000 or less.

[54] The component (A) according to any one of the above [50] to [53], wherein the final concentration of the compound represented by the formula (1) in the pharmaceutical composition is 0.01 w/v % or more and 80 w/v % or less, 0.1 w/v % or more and 10 w/v % or less, 0.5 w/v % or more and 5 w/v % or less, or 1 w/v %.

[55] The component (A) according to any one of the above [50] to [54], wherein the final concentration of the component (A) in the pharmaceutical composition is 0.01 w/v % or more and 60 w/v % or less, 0.01 w/v % or more and 30 w/v % or less, 1 w/v % or more and 15 w/v % or less, or 2 w/v % or more and less than 10 w/v %.

[56] The component (A) according to any one of the above [50] to [55], wherein the joint disease is osteoarthritis or rheumatoid arthritis.

[57] A method for treating a human joint disease, including a step of administering a pharmaceutical composition to a joint of a patient with a joint disease, wherein the pharmaceutical composition contains an effective amount of a compound represented by the following formula (1) and a component (A), wherein the component (A) is at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

[Chem. 1]

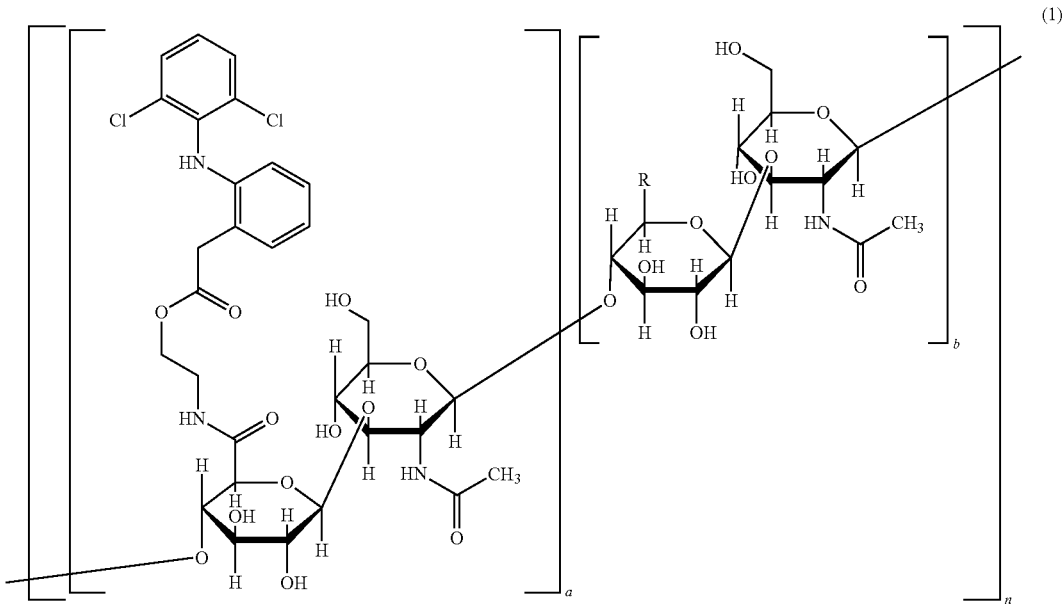

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

[58] The method according to the above [57], wherein the component (A) is selected from the group consisting of a nonionic surfactant, a hydroxyalkylated cyclodextrin, a $C_1$ to $C_3$ mono-alcohol, and a polyalkylene glycol.

[59] The method according to the above [57] or [58], wherein the polyalkylene glycol is polyethylene glycol.

[60] The method according to the above [59], wherein the weight average molecular weight of polyethylene glycol is 200 or more and 6,000 or less.

[61] The method according to any one of the above [57] to [60], wherein the concentration of the compound represented by the formula (1) in the pharmaceutical composition is 0.01 w/v % or more and 80 w/v % or less, 0.1 w/v % or more and 10 w/v % or less, 0.5 w/v % or more and 5 w/v % or less, or 1 w/v %.

[62] The method according to any one of the above [57] to [61], wherein the concentration of the component (A) in the pharmaceutical composition is 0.01 w/v % or more and 60 w/v % or less, 0.01 w/v % or more and 30 w/v % or less, 1 w/v % or more and 15 w/v % or less, or 2 w/v % or more and less than 10 w/v %.

[63] The method according to any one of the above [57] to [62], wherein the joint disease is osteoarthritis or rheumatoid arthritis.

EXAMPLES

Hereinafter, preferred embodiments of the present invention will be described in more detail using Examples, however, the present invention is by no means limited to the following Examples.

Synthesis Example

A hyaluronic acid derivative (a compound represented by the formula (1)) was synthesized in accordance with the method described in Examples of WO 2005/066214 (a: 0.18, n: 2000, mass average molecular weight of hyaluronic acid: 800,000).

More specifically, the synthesis was carried out by the following method.

2.155 g (10.5 mmol) of 2-bromoethylamine hydrobromide was dissolved in 20 mL of dichloromethane, and 1.463 mL (10.5 mmol) of triethylamine was added thereto under ice-cooling, and further 5 mL of a dichloromethane solution of 2.299 g (10.5 mmol) of di-tert-butyl-dicarbonate ($Boc_2O$) was added thereto, followed by stirring. After stirring at room temperature for 90 minutes, ethyl acetate was added thereto, and the resulting mixture was washed sequentially with a 5 wt % citric acid aqueous solution, water, and saturated brine. After dehydration with sodium sulfate, the solvent was distilled off under reduced pressure, whereby Boc-aminoethyl bromide was obtained.

5 mL of a dimethylformamide (DMF) solution of 2.287 g (10.2 mmol) of the thus obtained Boc-aminoethyl bromide was ice-cooled, and 6 mL of a DMF solution of 3.255 g (10.2 mmol) of diclofenac sodium was added thereto, followed by stirring overnight at room temperature. Stirring was performed at 60° C. for 11 hours, and then stirring was performed overnight at room temperature. Ethyl acetate was added thereto, and the resulting mixture was washed sequentially with a 5 wt % sodium hydrogen carbonate aqueous solution, water, and saturated brine. After dehydration with sodium sulfate, ethyl acetate was distilled off under reduced pressure. The residue was purified by silica gel column chromatography (toluene:ethyl acetate=20:1 (v/v), 0.5 vol % triethylamine), whereby Boc-aminoethanol-diclofenac was obtained.

2.108 g (4.80 mmol) of the thus obtained Boc-aminoethanol-diclofenac was dissolved in 5 mL of dichloromethane, and 20 mL of 4 M hydrochloric acid/ethyl acetate was added thereto under ice cooling, followed by stirring for 2.5 hours. Diethyl ether and hexane were added thereto to cause precipitation, and the precipitate was dried under reduced pressure. As a result, aminoethanol-diclofenac hydrochloride was obtained. The structure was identified by $^1$H-NMR.

$^1$H-NMR (500 MHz, CDCl$_3$) δ (ppm)=3.18 (2H, t, NH$_2$CH$_2$CH$_2$O—), 3.94 (2H, s, Ph-CH$_2$—CO), 4.37 (2H, t, NH$_2$CH$_2$CH$_2$O—), 6.47-7.31 (8H, m, Aromatic H, NH)

After 500 mg (1.25 mmol/disaccharide unit) of hyaluronic acid having a mass average molecular weight of 800,000 was dissolved in water (56.3 mL)/dioxane (56.3 mL), hydroxysuccinimide (1 mmol)/water (0.5 mL), water-soluble carbodiimide hydrochloride (WSCI.HCl) (0.5 mmol)/water (0.5 mL), and aminoethanol-diclofenac hydrochloride (0.5 mmol) obtained above/(water:dioxane=1:1 (v/v) (5 mL)) were sequentially added thereto, followed by stirring for a whole day and night. To the reaction solution, 7.5 mL of a 5 wt % sodium hydrogen carbonate aqueous solution was added, followed by stirring for about 4 hours. The reaction solution was neutralized by adding 215 μL of a 50% (v/v) acetic acid aqueous solution thereto, and then 2.5 g of sodium chloride was added thereto, followed by stirring. 400 mL of ethanol was added thereto to cause precipitation, and the precipitate was washed twice with an 85% (v/v) ethanol aqueous solution, twice with ethanol, and twice with diethyl ether, and then dried under reduced pressure overnight at room temperature, whereby a hyaluronic acid derivative (sodium salt) (a compound represented by the formula (1)) was obtained. The introduction ratio of diclofenac measured by a spectrophotometer was 18 mol %.

In addition, a dry material of a hyaluronic acid derivative (sodium salt) having an introduction ratio of 18 mol % was prepared according to the above Synthesis Example.

<Preparation of Test Sample>
Preparation of Phosphate Buffer Solution

A sodium dihydrogen phosphate aqueous solution having a phosphate concentration of 75 mM and a disodium hydrogen phosphate aqueous solution having a phosphate concentration of 75 mM were mixed at a ratio (volume ratio) of 17:11, whereby a phosphate buffer solution was prepared. The pH of the phosphate buffer solution after preparation was 6.5.

Preparation of Citrate Buffer Solution

A citric acid aqueous solution having a citric acid concentration of 15 mM and a trisodium citrate aqueous solution having a citrate concentration of 15 mM were mixed at a ratio (volume ratio) of 27:37, whereby a citrate buffer solution was prepared. The pH of the citrate buffer solution after preparation was 5.1.

Preparation of Acetate Buffer Solution

An acetic acid aqueous solution having an acetic acid concentration of 15 mM and a sodium acetate aqueous solution having an acetate concentration of 15 mM were mixed at a ratio (volume ratio) of 1:3, whereby an acetate buffer solution was prepared. The pH of the acetate buffer solution after preparation was 5.1. In addition, an acetate buffer solution having an acetic acid concentration of 45 mM and a pH of 5.1 was prepared in a similar manner.

Preparation of 1.5 wt % Hyaluronic Acid Derivative Solution 1.5 g of the hyaluronic acid derivative of the above Synthesis Example and 98.5 g of each of the various buffer solutions prepared above were mixed and stirred for 2 hours in a water bath at 70° C., whereby a 1.5 wt % hyaluronic acid derivative solution was prepared.

Preparation of Various Additional Component Aqueous Solutions

Additional component aqueous solutions to be added to the hyaluronic acid derivative solution were prepared using various additional components and WFI so that the concentration of each component is three times as high as the final concentration (wt %).

Preparation of Test Sample 2.0 g of the 1.5 wt % hyaluronic acid derivative solution prepared above and 1.0 g of the additional component aqueous solution were mixed, whereby a test sample (final concentration of hyaluronic acid derivative: 1.0 wt %) was prepared. In addition, a control solution that does not contain the additional component was prepared by mixing 1.0 g of WFI in place of 1.0 g of the additional component aqueous solution.

Example 1: Effect of Additional Component on Accumulation of Diclofenac Component The test samples prepared above containing each of the various buffer solutions (50 mM phosphate buffer solution, 10 mM citrate buffer solution, 10 mM acetate buffer solution, or 30 mM acetate buffer solution) were subjected to a storage test.

Each of the test samples was stored for 1 week in a thermostat chamber at 60° C., and thereafter, the accumulation amount of each of diclofenac and diclofenac lactam was measured by HPLC.

The amount of diclofenac and the amount of diclofenac lactam were calculated as relative values when each of the amount of diclofenac and the amount of diclofenac lactam present in the control solution (1 wt % hyaluronic acid derivative solution) after being stored for 1 week at 60° C. was assumed to be 1.

A more specific procedure of the storage test is as follows.
<Storage Test>

Each of the prepared various test samples was filled in a screw vial (AS ONE Corporation, Cat No. 3-1599-01) and left to stand at 60° C. for 1 week. The amount of diclofenac and the amount of diclofenac lactam present in the solution after being left to stand were quantitatively analyzed by HPLC.

The HPLC conditions are as follows.
Column: TSGgel ODS-100Z (4.6 mm×150 mm)
Flow rate: 1 mL/min
Temperature: 35° C.
Gradient: acetonitrile (B)/20 mM sodium phosphate (A)
B conc. (mL/min)
0.40 (0 min)-0.80 (30 min)
0.80 (33 min)-0.40 (35 min)

The elution time of each of diclofenac and diclofenac lactam was determined by performing measurement in advance using a standard substance.

Note that one week storage at 60° C. corresponds to one year storage at 25° C.
(1-1) Storage Test when Using 50 mM Phosphate Buffer Solution (pH 6.5)

As the additional component, L-arginine hydrochloride (final concentration in test sample: 3 wt %), L-methionine, L-lysine hydrochloride (3 wt %), α-cyclodextrin, β-cyclodextrin, γ-cyclodextrin, allyloxy-1,2-propanediol, sodium edetate (3 wt %), glycine, diglycerol, sodium thioglycolate (3 wt %), tetrakis(4-arboxyphenyl)porphyrin (1.5 wt %), nicotinamide, butylhydroxyanisole, phlorizin hydrate (1.5 wt %), benzyl alcohol, boric acid, polyvinyl alcohol (1.5 wt %), D-erythronolactone, D-glucal, PEG 200, PEG 4000, sodium erythorbate (3 wt %), or glycerin was used. The additional components whose concentration is not stated were all used at a final concentration of 5 wt %.
<Results>
When any one of L-arginine hydrochloride, L-methionine, L-lysine hydrochloride, α-cyclodextrin, β-cyclodextrin, γ-cyclodextrin, allyloxy-1,2-propanediol, sodium edetate, glycine, diglycerol, sodium thioglycolate, tetrakis(4-arboxyphenyl)porphyrin, nicotinamide, butylhydroxyanisole, phlorizin hydrate, benzyl alcohol, boric acid, and polyvinyl alcohol was used as the additional component, the amount of diclofenac lactam (relative value) exceeded 1 in all cases. That is, the generation amount of diclofenac lactam increased as compared with the control in which the additional component was not used, and promotion of the generation of diclofenac lactam was observed. When these additional components were used, the amount of diclofenac (relative value) exceeded 1 in all cases except the example of butylhydroxyanisole. The amount of diclofenac (relative value) in the case of butylhydroxyanisole was 0.99, and the effect as the additional component on the generation of diclofenac was almost not observed.

On the other hand, when any one of D-erythronolactone, D-glucal, PEG 200, PEG 4000, sodium erythorbate, and glycerin was used as the additional component, the amount of diclofenac lactam (relative value) was below 1 in all cases. That is, the generation amount of diclofenac lactam decreased as compared with the control in which the additional component was not used, and suppression of the generation of diclofenac lactam was observed (Table 1).

Since the generation of diclofenac lactam that has no practical activity as a COX-2 inhibitor is suppressed, it was revealed that D-erythronolactone, D-glucal, PEG 200, PEG 4000, sodium erythorbate, and glycerin can suppress the accumulation of diclofenac lactam. Further, in the case of D-erythronolactone and sodium erythorbate among these, the amount of diclofenac (relative value) was also below 1, and therefore, it was found that these components also suppress the accumulation of diclofenac.

TABLE 1

| Additional component | Final concentration (wt %) | Lac amount* | Dic amount** |
|---|---|---|---|
| D-erythronolactone | 5 | 0.47 | 0.72 |
| D-glucal | 5 | 0.89 | 1.15 |
| PEG 200 | 5 | 0.73 | 1.03 |
| PEG 4000 | 5 | 0.85 | 1.02 |
| sodium erythorbate | 3 | 0.48 | 0.81 |
| glycerin | 5 | 0.64 | 1.02 |

*Lac amount: the relative value of the amount of diclofenac lactam
**Dic amount: the relative value of the amount of diclofenac
(1-2) Storage Test when Using 10 mM Citrate Buffer Solution (pH 5.1)

As the additional component, creatinine (1 wt %), sodium deoxycholate (5 wt %), 1,2,3-butanetriol (5 wt %), PEG 400 (6.3 wt % or 16.5 wt %), PEG 600 (10 wt %), PEG 4000 (10 wt %), PEG 6000 (10 wt %), SDS (5 wt %), Triton X-100 (5 wt %), ethanol (26 wt %), octyl glucoside (5 wt %), glucuronolactone (0.1 wt %), chlorogenic acid (0.1 wt %), propylene glycol (10 wt %), polysorbate 20 (5 wt %), or polyvinylpyrrolidone (5 wt %) was used.

Similarly, as the additional component, additional components of a two-component system of PEG 3350 (10.6 wt %) and polysorbate 80 (3 wt %), or PEG 3350 (6.0 wt %) and hydroxypropyl-β-cyclodextrin (10 wt %), or additional components of a three-component system of PEG 3350 (5.5 wt %), polysorbate 80 (1 wt %) and hydroxypropyl-β-cyclodextrin (10 wt %) were used.
<Results>
When creatinine or sodium deoxycholate was used as the additional component, the amount of diclofenac lactam (relative value) exceeded 1 in both cases. That is, the generation amount of diclofenac lactam increased as compared with the control in which the additional component was not used, and promotion of the generation of diclofenac lactam was observed. When these additional components were used, the amount of diclofenac (relative value) also exceeded 1 in both cases.

On the other hand, when any one of 1,2,3-butanetriol, PEG 400, PEG 600, PEG 4000, PEG 6000, SDS, Triton X-100, ethanol, octyl glucoside, glucuronolactone, chlorogenic acid, propylene glycol, polysorbate 20, and polyvinylpyrrolidone was used as the additional component, the amount of diclofenac lactam (relative value) was below 1 in all cases. That is, the generation amount of diclofenac lactam decreased as compared with the control in which the additional component was not used, and suppression of the generation of diclofenac lactam was observed (Table 2). Table 2 also shows the solution properties after storage. As for the solution properties, the solution was colorless and clear in many cases, and even when it was colored, it was slightly yellowish, and even when it was not clear, it was slightly turbid. Further, when the above-mentioned two-component system or three-component system was used, the amount of diclofenac lactam (relative value) and the amount of diclofenac (relative value) were both below 1 in both cases. In addition, as for the solution properties of the two-component system and the three-component system, the solution was colorless and clear in both cases (Table 3).

Since the generation of diclofenac lactam that has no practical activity as a COX-2 inhibitor is suppressed, it was revealed that 1,2,3-butanetriol, PEG 400, PEG 600, PEG 4000, PEG 6000, SDS, Triton X-100, ethanol, octyl glucoside, glucuronolactone, chlorogenic acid, propylene glycol, polysorbate 20, and polyvinylpyrrolidone can be used as an agent for suppressing the accumulation of diclofenac lactam. Moreover, when using these components, the amount of diclofenac (relative value) was also below 1, and therefore, it was found that these components also suppress the accumulation of diclofenac.

TABLE 2

| Additional component | Final concentration (wt %) | Lac amount* | Dic amount** | Solution properties |
|---|---|---|---|---|
| 1,2,3-butanetriol | 5 | 0.50 | 0.93 | light yellow and slightly turbid |
| PEG 400 | 6.3 | 0.75 | 0.90 | colorless and clear |
| PEG 400 | 16.5 | 0.72 | 0.88 | colorless and clear |

TABLE 2-continued

| Additional component | Final concentration (wt %) | Lac amount* | Dic amount** | Solution properties |
|---|---|---|---|---|
| PEG 600 | 10 | 0.85 | 0.93 | colorless and clear |
| PEG 4000 | 10 | 0.45 | 0.64 | colorless and clear |
| PEG 6000 | 10 | 0.81 | 0.88 | colorless and clear |
| SDS | 5 | 0.55 | 0.97 | colorless and clear |
| Triton X-100 | 5 | 0.47 | 0.52 | colorless and clear |
| ethanol | 26 | 0.46 | 0.71 | colorless and clear |
| octyl glucoside | 5 | 0.30 | 0.55 | colorless and clear |
| glucuronolactone | 0.1 | 0.29 | 0.69 | slightly yellow and clear |
| chlorogenic acid | 0.1 | 0.37 | 0.77 | light yellow and clear |
| propylene glycol | 10 | 0.73 | 0.95 | colorless and slightly turbid |
| polysorbate 20 | 5 | 0.73 | 0.76 | colorless and clear |
| polyvinylpyrrolidone | 5 | 0.35 | 0.71 | light yellow and clear |

*Lac amount: the relative value of the amount of diclofenac lactam
**Dic amount: the relative value of the amount of diclofenac

TABLE 3

| Additional component | Final concentration (wt %) | Lac amount* | Dic amount** | Solution properties |
|---|---|---|---|---|
| PEG 3350 polysorbate 80 | 10.6 3 | 0.28 | 0.47 | colorless and clear |
| PEG 3350 HP-β-CD | 6.0 10 | 0.18 | 0.42 | colorless and clear |
| PEG 3350 polysorbate 80 HP-β-CD | 5.5 1 10 | 0.18 | 0.38 | colorless and clear |

*Lac amount: the relative value of the amount of diclofenac lactam
**Dic amount: the relative value of the amount of diclofenac (1-3) Storage Test when Using 30 mM Acetate Buffer Solution (pH 5.1)

As the additional component, propyl gallate (1.5 wt %), any one of lactic acid anhydrous (1.5 wt %), hydroxypropyl cellulose (1.5 wt %), starch (1.5 wt %), dextran (5 wt %), sucrose (5 wt %), sodium saccharinate dihydrate (5 wt %), glycine (5 wt %), sodium aspartate (1.5 wt %), L-leucine (1.5 wt %), L-phenylalanine (5 wt %), L-serine (5 wt %), D-mannitol (1.5 wt %), D-sorbitol (5 wt %), hydroxypropyl-β-cyclodextrin (3 wt %, 5 wt %, 10 wt %, or 15 wt %), and ethanol (5 wt %, 10 wt %, 20 wt %, or 26.3 wt %) was used.
<Results>

When any one of propyl gallate, lactic acid anhydrous, hydroxypropyl cellulose, starch, dextran, sucrose, sodium saccharinate dihydrate, glycine, sodium aspartate, L-leucine, L-phenylalanine, L-serine, D-mannitol, and D-sorbitol was used as the additional component, the amount of diclofenac lactam (relative value) exceeded 1 in all cases. That is, the generation amount of diclofenac lactam increased as compared with the control in which the additional component was not used, and promotion of the generation of diclofenac lactam was observed. When these additional components were used, the amount of diclofenac (relative value) also exceeded 1 in all cases.

On the other hand, when hydroxypropyl-β-cyclodextrin (HP-β-CD) or ethanol was used as the additional component, the amount of diclofenac lactam (relative value) was below 1 in both cases. That is, the accumulation amount of diclofenac lactam decreased as compared with the control in which the additional component was not used, and suppression of the accumulation of diclofenac lactam was observed (Table 4).

Since the generation of diclofenac lactam that has no practical activity as a COX-2 inhibitor is suppressed, it was revealed that hydroxypropyl-β-cyclodextrin and ethanol can be used as an agent for suppressing the accumulation of diclofenac lactam. Moreover, when using these components, the amount of diclofenac (relative value) was also below 1, and therefore, it was found that these components also suppress the accumulation of diclofenac.

TABLE 4

| Additional component | Final concentration (wt %) | Lac amount* | Dic amount** |
|---|---|---|---|
| HP-β-CD | 3 | 0.45 | 0.62 |
| HP-β-CD | 5 | 0.34 | 0.54 |
| HP-β-CD | 10 | 0.23 | 0.44 |
| HP-β-CD | 15 | 0.17 | 0.36 |
| ethanol | 5 | 0.89 | 0.93 |
| ethanol | 10 | 0.77 | 0.87 |
| ethanol | 20 | 0.60 | 0.81 |
| ethanol | 26.3 | 0.54 | 0.80 |

*Lac amount: the relative value of the amount of diclofenac lactam
**Dic amount: the relative value of the amount of diclofenac (1-4) Storage Test when Using 10 mM Acetate Buffer Solution (pH 5.1)

As the additional component, hydroxyethyl-β-cyclodextrin (5 wt %), PEG 400 (7.5 wt %), PEG 4000 (5 wt % or 15 wt %), ethanol (10 wt %), octyl glucoside (5 wt %), polysorbate 80 (5 wt % or 10 wt %), or polyvinylpyrrolidone (5 wt %) was used.
<Results>

When any one of hydroxyethyl-β-cyclodextrin (HP-β-CD), PEG 400, PEG 4000, ethanol, octyl glucoside, polysorbate 80, and polyvinylpyrrolidone was used as the additional component, the amount of diclofenac lactam (relative value) was below 1 in all cases. That is, the accumulation amount of diclofenac lactam decreased as compared with the control in which the additional component was not used, and suppression of the accumulation of diclofenac lactam was observed (Table 5).

Since the generation of diclofenac lactam that has no practical activity as a COX-2 inhibitor is suppressed, it was revealed that hydroxypropyl-β-cyclodextrin, PEG 400, PEG 4000, ethanol, octyl glucoside, polysorbate 80, and polyvinylpyrrolidone can be used as an agent for suppressing the accumulation of diclofenac lactam. Moreover, when using these components, the amount of diclofenac (relative value) was also below 1, and therefore, it was found that these components also suppress the accumulation of diclofenac.

TABLE 5

| Additional component | Final concentration (wt %) | Lac amount* | Dic amount** |
|---|---|---|---|
| HE-β-CD | 5 | 0.34 | 0.63 |
| PEG 400 | 7.5 | 0.76 | 0.90 |
| PEG 4000 | 5 | 0.56 | 0.76 |
| PEG 4000 | 15 | 0.34 | 0.56 |
| ethanol | 10 | 0.74 | 0.89 |
| octyl glucoside | 5 | 0.24 | 0.72 |
| polysorbate 80 | 5 | 0.86 | 0.65 |
| polysorbate 80 | 10 | 0.81 | 0.62 |
| polyvinylpyrrolidone | 5 | 0.36 | 0.72 |

*Lac amount: the relative value of the amount of diclofenac lactam
**Dic amount: the relative value of the amount of diclofenac <Conclusion>

Through these Examples, it was confirmed that polysorbate 20, polysorbate 80, Triton X-100, octyl glucoside, hydroxyethyl-β-cyclodextrin, hydroxypropyl-β-cyclodextrin, ethanol, glycerin, 1,2,3-butanetriol, D-glucal, PEG 200, PEG 400, PEG 600, PEG 4000, PEG 6000, D-erythronolactone, sodium erythorbate, glucuronolactone, polyvinylpyrrolidone, chlorogenic acid, SDS, and propylene glycol have an effect of suppressing the accumulation of diclofenac lactam.

Therefore, a nonionic surfactant such as polysorbate 20, polysorbate 80, Triton X-100, or octyl glucoside; a hydroxyalkylated cyclodextrin such as hydroxyethyl-β-cyclodextrin or hydroxypropyl-β-cyclodextrin; a $C_1$ to $C_3$ mono-alcohol such as ethanol; a $C_2$ to $C_3$ di-alcohol such as propylene glycol; a $C_3$ to $C_6$ tri-alcohol such as glycerin, 1,2,3-butanetriol, or D-glucal; a polyalkylene glycol such as PEG 200, PEG 400, PEG 600, PEG 4000, or PEG 6000; a γ-lactone such as D-erythronolactone, sodium erythorbate, or glucuronolactone; polyvinylpyrrolidone, a chlorogenic acid such as chlorogenic acid, and an alkyl sulfate ester such as SDS can be used as an agent for suppressing the generation of diclofenac lactam from a hyaluronic acid derivative, and also as an agent for suppressing the accumulation of diclofenac lactam in a pharmaceutical composition containing a hyaluronic acid derivative. In addition, pharmaceutically acceptable salts thereof can also be used similarly.

Example 2: Evaluation of Filterability of Aqueous Composition

With respect to hydroxypropyl-β-cyclodextrin (HP-β-CD), ethanol, PEG 400, and PEG 4000, filtration of an aqueous composition containing a hyaluronic acid derivative was examined.

<Preparation of Test Sample>

Preparation of 1.5 wt % Hyaluronic Acid Derivative Solution

The hyaluronic acid derivative prepared above and the 15 mM acetate buffer solution (pH 5.1) prepared above were mixed and stirred, and then, defoamed by being left to stand, whereby a 1.5 wt % hyaluronic acid derivative solution was prepared.

Preparation of Test Sample 150.0 g of the 1.5 wt % hyaluronic acid derivative solution prepared above and 75.0 g of an additional component aqueous solution were mixed, whereby a test sample (final concentration of hyaluronic acid derivative: 1.0 wt %) was prepared.

In addition, a control solution in which 75.0 g of WFI was mixed in place of the additional component aqueous solution was also prepared.

<Test Method for Filterability>

To a stainless steel pressure filter holder in which a polyvinylidene fluoride (PVDF) membrane (47 mm in diameter, effective filtration area: 13.8 $cm^2$, manufactured by Merck & Co.) with a pore size of 0.22 μm was set, 200 mL of the test sample prepared above was added and pressure was applied at 0.6 MPa at 70° C. The amount of liquid passing through the filter was weighed every 30 seconds, and the maximum treatment amount ($V_{max}$) was calculated from the relationship between the elapsed time and the total filtration amount.

<Results>

It was confirmed that when the additional components were used, the maximum treatment amount ($V_{max}$) was 1.0 g/$cm^2$ or more in all cases (Table 6). Above all, in the case of PEG 400, the maximum treatment amount ($V_{max}$) was a high value.

TABLE 6

| Additional component | Final concentration (wt %) | Maximum treatment amount (g/$cm^2$) |
|---|---|---|
| (Control solution) | — | 0.5 |
| PEG 400 | 5 | 20.6 |
| PEG 400 | 10 | 5.1 |
| PEG 400 | 20 | 3.4 |
| PEG 4000 | 5 | 5.6 |
| PEG 4000 | 10 | 5.5 |
| PEG 4000 | 20 | 1.6 |
| ethanol | 5 | 10.3 |
| ethanol | 10 | 8.2 |
| HP-β-CD | 5 | 8.3 |
| HP-β-CD | 10 | 10.4 |

<Conclusion>

At the time of filter filtration, if the filtration is stopped before the flow rate becomes 1/10 of the initial flow rate, the filter cannot be used effectively, and if it is used more than this, a long filtration time is needed, which is not preferred in terms of work efficiency. The V90 value calculated as a value obtained by multiplying the $V_{max}$ value by 0.68 (the reduction ratio of the filter processing capacity when the flow rate becomes 1/10 of the initial flow rate is assumed to be 68%) corresponds to the processing amount until the time when the flow rate becomes 1/10 of the initial flow rate. It is known empirically that the V90 value is a preferred value when evaluating the filterable amount (if necessary, see "Vmax Test, Filter Selection and Optimization Methods", written by Kimihiko Kobayashi, Bioprocess Technical Sheet, Basic Technique No. 2, Japan Millipore, August, 1997). An aqueous composition that shows a maximum treatment amount ($V_max$) of 1.0 g/$cm^2$ or more as described above also shows a high V90 value and therefore can be said to have excellent filter filterability. That is, such an aqueous composition is suitable for mass production on an industrial scale because it is less likely to be clogged during filtration so that the frequency of replacement or washing of the filtration filter is low, and so on. Therefore, even when it is provided as a pharmaceutical composition, heat sterilization or the like is not needed. Accordingly, it can be provided as a composition in which the accumulation of a diclofenac component, especially the accumulation amount of diclofenac lactam is suppressed.

Example 3: Preparation of Pharmaceutical Composition

The component (A) is used in the preparation of a pharmaceutical composition together with a hyaluronic acid derivative. As an example, preparation of a pharmaceutical composition for injection containing a hyaluronic acid derivative, PEG 400, and a citrate buffer solution will be shown.

(Step 1) Predetermined amounts of citric acid hydrate, disodium citrate hydrate, and PEG 400 are dissolved in WFI.

(Step 2) A predetermined amount of a hyaluronic acid derivative (introduction ratio: 18 mol %) is dissolved in the solution of Step 1. Then, the solution after dissolution is heated to 70° C. and degassed by heating under reduced pressure.

(Step 3) The solution of Step 2 is sterilized by filtration through a filter with a pore size of 0.22 μm.

(Step 4) The solution of Step 3 is degassed by heating at 70° C., and then cooled to 10° C.

(Step 5) A predetermined amount is filled in a syringe under sterilization conditions.

By the above (Step 1) to (Step 5), a sterilized pharmaceutical composition containing a hyaluronic acid derivative, PEG 400, and a citrate buffer solution is prepared. Here, as the concentrations of the respective components, the hyaluronic acid derivative: 0.5 to 5 w/v %, PEG 400: 3 to 30 w/v %, and the citrate buffer solution: 3 to 30 mM (in terms of citric acid) are exemplified, however, the concentrations of the various components in the pharmaceutical composition are not limited to the above respective ranges.

INDUSTRIAL APPLICABILITY

The present invention provides, for example, a composition, which brings about a significant improving effect on a joint disease of a patient with a human joint disease (particularly, a patient with a chronic joint disease), and which has excellent stability such that the accumulation of diclofenac lactam that is a physiologically inactive component is suppressed, and therefore has industrial applicability in the pharmaceutical industry or the like.

While the present invention has been described in connection with specific Examples and various embodiments, many modifications and applications of the embodiments described herein may be made without departing from the spirit and scope of the invention as will be readily understood by a person skilled in the art.

The present application claims priority based on Japanese Patent Application No. 2018-215867 filed with the Japan Patent Office on Nov. 16, 2018, the contents of which are incorporated herein by reference in their entirety.

The invention claimed is:

1. A pharmaceutical composition, comprising a compound represented by the following formula (1) and a component (A):

the component (A): at least one type of compound selected from the group consisting of a nonionic surfactant, a hydroxyalkylated cyclodextrin, a $C_1$ to $C_3$ mono-alcohol, a $C_2$ to $C_3$ di-alcohol, a $C_3$ to $C_6$ tri-alcohol, a polyalkylene glycol, a γ-lactone, polyvinylpyrrolidone, a chlorogenic acid, and an alkyl sulfate ester, and salts thereof:

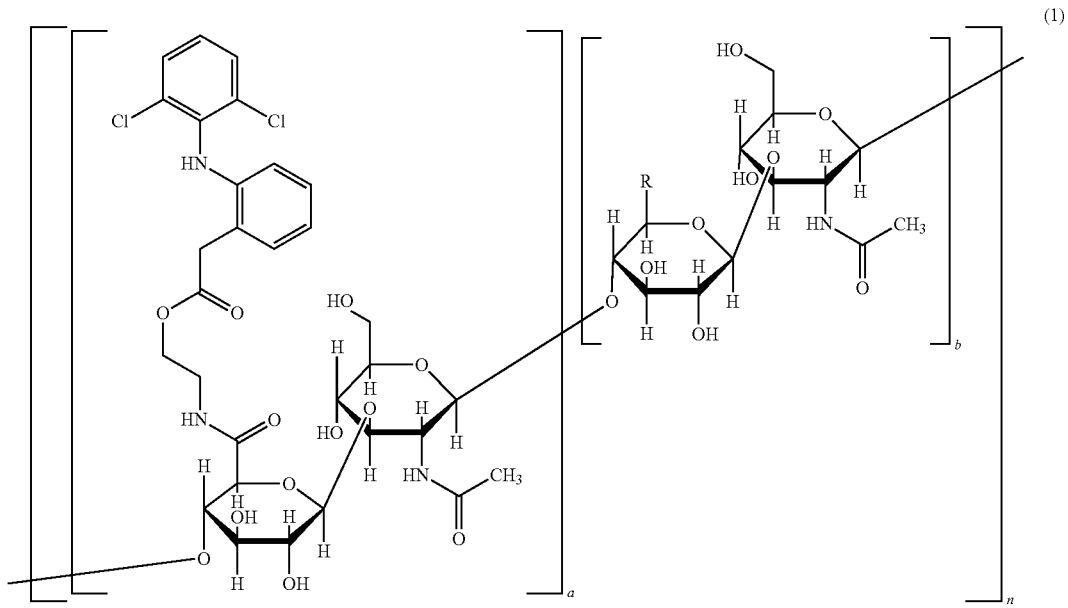

wherein a is 0.01 or more and 0.7 or less, a+b is 1, n is an integer of 25 or more and 25,000 or less, respective constituent disaccharide units may be arranged in a random or block form, and R is each independently a carboxy group or a carboxylate salt group in the respective constituent disaccharide unit.

2. The pharmaceutical composition according to claim 1, wherein the component (A) is selected from the group consisting of a nonionic surfactant, a hydroxyalkylated cyclodextrin, a $C_1$ to $C_3$ mono-alcohol, and a polyalkylene glycol.

3. The pharmaceutical composition according to claim 1, wherein the polyalkylene glycol is polyethylene glycol.

4. The pharmaceutical composition according to claim 3, wherein the weight average molecular weight of polyethylene glycol is 200 or more and 6,000 or less.

5. The pharmaceutical composition according to claim 1, wherein the final concentration of the component (A) is from 0.01 to 30 wt %.

6. The pharmaceutical composition according to claim 1, further comprising a buffer solution selected from the group consisting of a phosphate buffer solution, a citrate buffer solution, and an acetate buffer solution.

7. The pharmaceutical composition according to claim 1, wherein the pH is from 4.5 to 7.0.

8. The pharmaceutical composition according to claim 1, which is an aqueous composition.

9. The pharmaceutical composition according to claim 1, which is a pharmaceutical composition for treating a joint disease.

10. The pharmaceutical composition according to claim 9, wherein the joint disease is osteoarthritis or rheumatoid arthritis.

11. A kit, comprising an injector in which the pharmaceutical composition according to claim 1 is filled in a syringe barrel.

12. A kit, comprising a vial containing the pharmaceutical composition according to claim 1, and an injector.

13. The pharmaceutical composition according to claim 1, wherein a mass average molecular weight of a hyaluronic acid in the compound represented by the formula (1) is 600,000 or more and 1,200,000 or less.

\* \* \* \* \*

UNITED STATES PATENT AND TRADEMARK OFFICE
CERTIFICATE OF CORRECTION

PATENT NO. : 11,744,899 B2
APPLICATION NO. : 17/276263
DATED : September 5, 2023
INVENTOR(S) : Chiaki Takahata et al.

It is certified that error appears in the above-identified patent and that said Letters Patent is hereby corrected as shown below:

On the Title Page

Item (56) References Cited, OTHER PUBLICATIONS, "aminolphenyl" should read --amino]phenyl--.

Item (56) References Cited, OTHER PUBLICATIONS, "derivatie" should read --derivative--.

In the Specification

Column 12, Lines 11-12, "diclofenaclactam" should read --diclofenac lactam--.

Column 12, Line 19, "diclofenaclactam" should read --diclofenac lactam--.

Column 14, Line 6, "ferroylquinic" should read --feruloylquinic--.

Column 19, Line 43, "($V_m$ax)" should read --($V_{max}$)--.

Column 38, Line 64, "tetrakis(4-arboxyphenyl)porphyrin" should read --tetrakis(4-carboxyphenyl)porphyrin--.

Column 39, Lines 8-9, "tetrakis(4-arboxyphenyl)porphyrin," should read --tetrakis(4-carboxyphenyl)porphyrin,--.

Column 44, Line 50, "($V_m$ax)" should read --($V_{max}$)--.

Signed and Sealed this
Twenty-first Day of May, 2024

Katherine Kelly Vidal
*Director of the United States Patent and Trademark Office*